United States Patent
Yamamoto et al.

(10) Patent No.: US 10,214,743 B2
(45) Date of Patent: Feb. 26, 2019

(54) COLORECTAL CANCER DRUG, AND METHOD FOR PREDICTING PROGNOSIS OF COLORECTAL CANCER PATIENT

(71) Applicants: Hirofumi Yamamoto, Suita-shi, Osaka (JP); Masaki Mori, Suita-shi, Osaka (JP)

(72) Inventors: Hirofumi Yamamoto, Suita (JP); Masaki Mori, Suita (JP); Yuichiro Doki, Suita (JP); Junichi Nishimura, Suita (JP)

(73) Assignees: Hirofumi Yamamoto, Suita-shi, Osaka (JP); Masaki Mori, Suita-shi, Osaka (JP)

(*) Notice: Subject to any disclaimer, the term of this patent is extended or adjusted under 35 U.S.C. 154(b) by 0 days.

(21) Appl. No.: 15/123,621

(22) PCT Filed: Mar. 4, 2015

(86) PCT No.: PCT/JP2015/056354
§ 371 (c)(1),
(2) Date: Sep. 2, 2016

(87) PCT Pub. No.: WO2015/133522
PCT Pub. Date: Sep. 11, 2015

(65) Prior Publication Data
US 2017/0073686 A1 Mar. 16, 2017

(30) Foreign Application Priority Data
Mar. 4, 2014 (JP) .................. 2014-041768

(51) Int. Cl.
*A61K 31/7088* (2006.01)
*C12N 15/11* (2006.01)
*C12N 15/113* (2010.01)
*A61K 47/02* (2006.01)
*A61K 31/7105* (2006.01)
*C12Q 1/6886* (2018.01)
*A61K 47/48* (2006.01)
*A61K 9/00* (2006.01)
*A61K 9/51* (2006.01)

(52) U.S. Cl.
CPC ........ *C12N 15/1135* (2013.01); *A61K 9/0019* (2013.01); *A61K 9/5115* (2013.01); *A61K 31/7105* (2013.01); *A61K 47/02* (2013.01); *A61K 47/48861* (2013.01); *C12Q 1/6886* (2013.01); *C12N 2310/141* (2013.01); *C12N 2310/351* (2013.01); *C12Q 2600/118* (2013.01); *C12Q 2600/156* (2013.01); *C12Q 2600/158* (2013.01); *C12Q 2600/178* (2013.01)

(58) Field of Classification Search
CPC ............... A61K 31/7088; C12N 15/11; C12N 15/1135; C12N 2310/141
See application file for complete search history.

(56) References Cited

U.S. PATENT DOCUMENTS

| | | | |
|---|---|---|---|
| 2008/0039521 A1 | 2/2008 | Yasuda et al. | |
| 2009/0137683 A1 | 5/2009 | Yasuda et al. | |
| 2014/0302145 A1 | 10/2014 | Yamamoto et al. | |
| 2015/0337332 A1* | 11/2015 | Ruohoa-Baker | C12N 9/22 514/44 R |
| 2016/0017321 A1* | 1/2016 | Zhang | C12N 15/111 514/44 A |

FOREIGN PATENT DOCUMENTS

| | | |
|---|---|---|
| JP | 2008/239596 A | 10/2008 |
| JP | 2011/093892 A | 5/2011 |
| WO | WO 2013/109604 A1 | 7/2013 |
| WO | WO 2014/012081 A2 | 1/2014 |

OTHER PUBLICATIONS

Arrington, et al. 2012 "Prognostic and Predictive Roles of KRAS Mutation in Colorectal Cancer" *Int. J. Mol. Sci.* 13: 12153-12168.
Bokemeyer, et al. 2009 "Fluorouracil, Leucovorin, and Oxaliplatin With and Without Cetuximab in the First-Line Treatment of Metastatic Colorectal Cancer" *Journal of Clinical Oncology* 27(5): 663-671.
Corcoran, et al. 2013 "Synthetic Lethal Interaction of Combined BCL-XL and MEK Inhibition Promotes Tumor Regressions in KRAS Mutant Cancer Models" *Cancer Cell* 23: 121-128.
Hidekazu, et al. 2013 "The microRNAs for the diagnosis and treatment of upper gastrointestinal malignancy: application of appatite-nanocarrie" *Keio Associated Reposity of Academic Resources* in 7 pages.
Hiraki, et al. 2015 "Concurrent targeting of KRAS and AkT by MiR-4689 is a novel treatment against mutant KRAS colorectal cancer" *Molecular Therapy—Nucleic Acids* 4: 1-13.
Hiraki, et al. 2015 "Concurrent targeting of KRAS and AkT by MiR-4689 is a novel treatment against mutant KRAS colorectal cancer" *Nippon Bunshi Shuyo Marker Kenkyukaishi* (*Material and Method*) 30: 57-58.
International Search Report issued for International Application No. PCT/JP2015/056354, dated Jun. 9, 2015 (in 3 pages).
Liao, et al. 2014 "MicroRNA-30b functions as a tumour suppressor in human colorectal cancer by targeting KRAS, PIK3CD and BCL2" *Journal of Pathology* 232: 415-427.

(Continued)

*Primary Examiner* — Kevin K Hill
(74) *Attorney, Agent, or Firm* — Knobbe, Martens, Olson & Bear, LLP

(57) ABSTRACT

The purpose of the present invention is to provide a colorectal cancer drug that uses microRNA exhibiting outstanding effectiveness in colorectal cancer patients, particularly colorectal cancer patients having a mutated KRAS gene. miR4689 and/or miR4685-3p can suppress the growth of colorectal cancer cells, particularly colorectal cancer cells having a mutated KRAS gene, and thus exhibit an effective antitumor effect.

3 Claims, 21 Drawing Sheets

Specification includes a Sequence Listing.

(56) References Cited

OTHER PUBLICATIONS

Misale, et al. 2012 "Emergence of KRAS mutations and acquired resistance to anti-EGFR therapy in colorectal cancer" *Nature* 486: 532-536 (Plus Supplemental Methods Section).
Tsang, et al. 2009 "The miR-18a microRNA functions as a potential tumor suppressor by targeting on K-Ras" *Carcinogenesis* 30(6): 953-959.
Van Cutsem, et al. 2009 "Cetuximab and Chemotherapy as Initial Treatment for Metastatic Colorectal Cancer" *The New England Journal of Medicine* 360(14): 1408-1417.

* cited by examiner

Death and anti-death: tumour resistance to apoptosis
Frederik H. Igney & Peter H. Krammer
Nature Reviews Cancer 2, 277-288 (April 2002)

** $p<0.01$

|  | Parent | miR-NC | miR-4689 | p |
|---|---|---|---|---|
| TP (g/dl) | 5.3±0.17 | 5.4±0.09 | 5.7±0.06 | NS |
| Alb (g/dl) | 3.8±0.12 | 3.7±0.02 | 3.9±0.13 | NS |
| ALP (U/l) | 64±12.0 | 58±8.2 | 30±3.5 | NS |
| ALT (U/l) | 89±3.5 | 82±14.7 | 46±3.9 | NS |
| AMY (U/l) | 1024±63.9 | 1026±34.2 | 985±16.0 | NS |
| BUN (mg/dl) | 28.7±1.2 | 27.7±0.33 | 35.3±0.38 | 0.001 |
| Cre (mg/dl) | 0.2±0.06 | 0.23±0.03 | 0.23±0.03 | NS |
| Ca (mg/dl) | 10.4±0.58 | 10.2±0.24 | 10.7±0.23 | NS |
| P (mg/dl) | 8.2±0.77 | 8.3±0.74 | 7.8±1.3 | NS |
| Na (mmol/l) | 150±0.38 | 148±0.38 | 147±1.3 | NS |

(Day 14)

SEQUENCE LISTING

<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
uugaggagac auggugggggg cc                                           22

<210> SEQ ID NO 2
<211> LENGTH: 22
<212> TYPE: RNA
<213> ORGANISM: Homo sapiens

<400> SEQUENCE: 2
ucucccuucc ugcccuggcu ag                                            22

<210> SEQ ID NO 3
<211> LENGTH: 564
<212> TYPE: DNA
<213> ORGANISM: Homo sapiens

<400> SEQUENCE: 3
atgactgaat ataaacttgt ggtagttgga gctgttggcg taggcaagag tgccttgacg    60
atacagctaa ttcagaatca ttttgtggac gaatatgatc caacaataga ggattcctac   120
aggaagcaag tagtaattga tgagaaaacc tgtctcttgg atattctcga cacagcaggt   180
caagaggagt acagtgcaat gagggaccag tacatgagga ctggggaggg ctttcttttgt  240 gtatttgcca taaataatac taaatcattt gaagatattc accattatag agaacaaatt   300
aaaagagtta aggactctga agatgtacct atggtcctag taggaaataa atgtgatttg   360
ccttctagaa cagtagacac aaaacaggct caggacttag caagaagtta tggaattcct   420
tttattgaaa catcagcaaa gacaagacag ggtgttgatg atgccttcta tacattagtt   480
cgagaaattc gaaacataa agaaaagatg agcaaagatg gtaaaaagaa gaaaaagaag   540
tcaaagacaa agtgtgtaat tatg                                         564

<210> SEQ ID NO 4
<211> LENGTH: 21
<212> TYPE: RNA
<213> ORGANISM: Artificial Sequence
<220> FEATURE:
<223> OTHER INFORMATION: Control microRNA

<400> SEQUENCE: 4
auccgcgcga uaguacguau u                                             21

<210> SEQ ID NO 5
<211> LENGTH: 19
<212> TYPE: RNA
<213> ORGANISM: Artificial Sequence
<220> FEATURE:
<223> OTHER INFORMATION: Control microRNA

<400> SEQUENCE: 5
auccgcgcga uaguacgua                                                19

<210> SEQ ID NO 6
<211> LENGTH: 254
<212> TYPE: DNA
<213> ORGANISM: Artificial Sequence

```
<220> FEATURE:
<223> OTHER INFORMATION: Insert nucleic acid

<400> SEQUENCE: 6
tgtcatcttg cctccctacc ttccacatgc cccatgactt gatgcagttt taatacttgt    60
aattcccctg accataagat ttactgctgc tgtggatatc tccatgaagt tttcccactg   120
agtcacatca gaaatgccct acatcttatt tcctcagggc tcaagagaat ctgacagata   180
ccataaaggg atttgaccta atcactaatt ttcaggtggt ggctgatgct ttgaacatct   240
ctttgctgcc caat                                                     254

<210> SEQ ID NO 7
<211> LENGTH: 173
<212> TYPE: DNA
<213> ORGANISM: Artificial Sequence
<220> FEATURE:
<223> OTHER INFORMATION: Insert nucleic acid

<400> SEQUENCE: 7
atgagcgacg tggctattgt gaaggagggt tggctgcaca acgagggga gtacatcaag    60 acctggcggc cacgctactt cctcctcaag aatgatggca ccttcattgg ctacaaggag   120
cggcgcagga tgtggaccaa cgtgaggctc ccctcaacaa cttctctgtg gcg          173

<210> SEQ ID NO 8
<211> LENGTH: 22
<212> TYPE: RNA
<213> ORGANISM: Homo sapiens

<400> SEQUENCE: 8
gcccuacauc uuauuuccuc ag                                             22

<210> SEQ ID NO 9
<211> LENGTH: 22
<212> TYPE: RNA
<213> ORGANISM: Homo sapiens

<400> SEQUENCE: 9
ggccacgcua cuuccuccuc aa                                             22
```

COLORECTAL CANCER DRUG, AND METHOD FOR PREDICTING PROGNOSIS OF COLORECTAL CANCER PATIENT

TECHNICAL FIELD

The present invention relates to a therapeutic agent for colorectal cancer including microRNA. More specifically, the present invention relates to a therapeutic agent for colorectal cancer, the therapeutic agent including microRNA which has excellent efficacy on KRAS-mutant colorectal cancer. Further more specifically, the present invention relates to a method of predicting prognosis of a patient with colorectal cancer.

A Sequence Listing submitted as an ASCII text file via EFS-Web is hereby incorporated by reference in accordance with 35 U.S.C. § 1.52(e). The name of the ASCII text file for the Sequence Listing is 24143772_1.TXT, the date of creation of the ASCII text file is Sep. 2, 2016, and the size of the ASCII text file is 2.99 KB.

BACKGROUND ART

The EGFR (Epidermal growth factor receptor) is a tyrosine kinase receptor of the ER (ErbB) family. The EGFR is known to be playing important roles in cell differentiation, cell proliferation, and maintenance of the state of cells in normal tissue, and also, in carcinoma tissue, to be heavily involved in growth, invasion, and metastasis. Signal transduction downstream of the EGFR is carried out by KRAS.

Signal transduction downstream of RAS is mainly carried out via the RAF-MEK-ERK cascade. It is also carried out via the SEK-JNK cascade, in which SEK and JNK are members of the broad MAPK family, the PI3K-AKT cascade that is deeply involved in apoptosis, the DAG-PKC cascade, and the JAK-STAT cascade, for example. A signal from a receptor like EGFR is transduced via such a cascade into the nucleus, where the signal activates various transcriptional factors and induces proliferation, survival, invasion, and anti-apoptotic activity of the cells.

The KRAS gene is known as a colorectal cancer proto-oncogene. KRAS-gene mutation is found in about 40% of patients with colorectal cancer. Conventionally, colorectal cancer with wild-type KRAS gene is effectively treated by administration of an anti-EGFR antibody, such as cetuximab, that suppresses signal transduction from EGFR. This treatment has been a great success. However, the anti-EGFR antibody is known as being ineffective against KRAS-gene-mutant colorectal cancer (Non-patent Documents 1 and 2, for example). A reason for this ineffectiveness in KRAS-gene-mutant colorectal cancer is probably the following: RAS mutation causes a lack of GTPase; RAS is constitutively active; signals downstream of RAS are turned on at all times; proliferation, survival, invasion, and anti-apoptotic activity of the cell are further induced; and, as a result, the action of the anti-EGFR antibody is canceled.

According to reports, blocking the signals downstream of RAS has an antitumor effect on KRAS-gene-mutant colorectal cancer cells. For example, Patent Document 3 reports that a MEK1/2 inhibitor can suppress proliferation of KRAS-gene-mutant colorectal cancer cells. Patent Document 4 reports that the suppressive effect of a MEK1/2 inhibitor on proliferation of KRAS-gene-mutant colorectal cancer cells is enhanced when the MEK1/2 inhibitor is used in combination with cetuximab.

A microRNA is a small RNA molecule of 18 to 24 nucleotides and is found in a wide range of eukaryotes. About 1,000 human miRNAs have been found. The miRNA is a short, single-stranded, endogenously-expressed RNA molecule first reported in 1993. From DNA, an RNA molecule having a loop structure is transcribed, which is called pri-miRNA. The loop is cleaved by an enzyme to yield a pre-miRNA. The pre-miRNA is exported from the nucleus. Then, from the pre-miRNA, a miRNA sequence of 20 to 25 bases is cut out by Dicer. The miRNA sequence is taken in by an RNA-induced silencing complex (RISC), which is a complex of ribonucleic acid and protein Argonaute. As a result, a miRNA-RISC complex is formed, which binds to the 3'UTR of mRNA and suppresses gene expression. The pairing between a miRNA molecule and an mRNA molecule is not perfect, and therefore a single miRNA molecule can have more than one target genes. This means that a single miRNA molecule can be regulated by targeting a plurality of genes, which is an important feature of miRNA.

The expression pattern of microRNA in KRAS-gene-mutant colorectal cancer has not yet been identified. Therefore, if analysis on changes in microRNAs in KRAS-gene-mutant colorectal cancer caused by activation of signal transduction pathways induced by KRAS-gene mutation can successfully establish a treatment that corrects aberration of the microRNAs, patients with KRAS-gene-mutant colorectal cancer can be helped.

PRIOR ART DOCUMENTS

Non-Patent Documents

Non-Patent Document 1: Van Cutsem E, et al., N Engl J Med., 2009 Apr. 2; 360(14): 1408-17

Non-Patent Document 2: Bokemeyer C, et al., J Clin Oncol., 2009 Feb. 10: 27(5):663-71

Non-Patent Document 3: Cancer cell, 2013 Jan. 14; 23:121-128

Non-Patent Document 4: Misale S, et al., Nature, 2012 Jun. 28; 486(7404):532-6

SUMMARY OF THE INVENTION

Problems to be Solved by the Invention

An object of the present invention is to provide a therapeutic agent for colorectal cancer, the therapeutic agent including microRNA which has excellent efficacy on a patient with colorectal cancer, especially a patient with KRAS-gene-mutant colorectal cancer. Another object of the present invention is to provide a method of predicting prognosis of a patient with colorectal cancer.

Means for Solving the Problem

With intention to achieve these objects, and in order to exhaustively search for microRNAs that function downstream of KRAS, the inventors of the present invention have conducted exhaustive research on microRNA expression in normal human cells in which the one and only mutation is KRAS gene mutation. As a result, he has found significantly low expression of miR4689 or miR4685-3p in the cells compared to that obtained in normal cells with wild-type KRAS gene. Upon addition of miR4689 to KRAS-gene-mutant colorectal cancer cells, they have observed increases in the levels of apoptotic markers BAX BAD, and BAK and significantly suppressed proliferation. He has also found binding of miR4689, at least, to a site in the 3'UTR region of KRAS present upstream within the Ras/MEK/MAPK pathway and to a site in the CDS region of AKT1 in the PI3K/Akt pathway, indicating miR4689 targeting the KRAS gene and the AKT1 gene. They have further found poorer postsurgical prognosis of patients with colorectal cancer with low expression of miR4689 than that of patients with colorectal cancer with high expression of miR4689, indicating that the expression levels of miR4689 in patients with colorectal cancer can serve as an indicator for predicting postoperative prognosis of patients with colorectal cancer. He has further studied based on these findings and finally has completed the present invention.

The present invention provides an invention having the following embodiments.

Item 1. A therapeutic agent for colorectal cancer, including either one or both of miR4689 and miR4685-3p as an active ingredient.

Item 2. The therapeutic agent for colorectal cancer according to Item 1, wherein the therapeutic agent for colorectal cancer is applied to KRAS-gene-mutant colorectal cancer.

Item 3. The therapeutic agent for colorectal cancer according to Item 2, wherein the KRAS-gene-mutant colorectal cancer includes a RAS gene having amino acid substitution at either one or both of a codon 12 and a codon 13.

Item 4. The therapeutic agent for colorectal cancer according to any one of Items 1 to 3, wherein either one or both of the miR4689 and the miR4685-3p is in the form of complex with carbonate apatite particles.

Item 5. The therapeutic agent for colorectal cancer according to Item 4, wherein the average particle size of the carbonate apatite particles is 50 nm or less.

Item 6. A method of treating colorectal cancer, including a step of administering a therapeutically effective amount of either one or both of miR4689 and miR4685-3p to a patient with colorectal cancer.

Item 7. Use of either one or both of miR4689 and miR4685-3p for production of a therapeutic agent for colorectal cancer.

Item 8. Either one or both of miR4689 and miR4685-3p for use in treating colorectal cancer.

Item 9. A method of predicting prognosis of a patient with colorectal cancer, including a step of detecting the expression amount of miR4689 in a colorectal cancer cell derived from a patient with colorectal cancer.

Item 10. A marker for predicting prognosis of a patient with colorectal cancer, including miR4689.

Advantages of the Invention

The therapeutic agent for colorectal cancer of the present invention can suppress proliferation of KRAS-gene-mutant colorectal cancer cells with either one or both of miR4689 and miR4685-3p, and therefore can effectively treat KRAS-gene-mutant colorectal cancer that is not effectively treated by administration of an anti-EGFR antibody. The mechanism by which the therapeutic agent for colorectal cancer of the present invention, in particular, exhibits its therapeutic effect on KRAS-gene-mutant colorectal cancer is probably, but is not intended to be limited to, the following: miR4689 targets, at least, the KRAS gene in the Ras/MEK/MAPK pathway and the AKT1 gene in the PI3K/Akt pathway and translationally suppresses their expression; and, as a result, the therapeutic effect on KRAS-gene-mutant colorectal cancer is exhibited.

In addition, the therapeutic agent for colorectal cancer of the present invention includes complex particles of either one or both of miR4689 and miR4685-3p and carbonate apatite. In the form of the complex particles, either one or both of the miR4689 and the miR4685-3p after administration into a living organism can be made accumulated on colorectal cancer cells and efficiently transferred into the colorectal cancer cells. Such DDS capability is required in practical treatment of colorectal cancer. In addition to this, the therapeutic agent for colorectal cancer of the present invention is also highly safe. Therefore, the therapeutic agent for colorectal cancer of the present invention has immense clinical benefit.

Moreover, the method of predicting prognosis of a patient with colorectal cancer of the present invention uses expression levels of miR4689 in colorectal cancer cells as an indicator, which allows estimation of whether postsurgical prognosis of the colorectal cancer is likely to become worse. By this method, prompt and suitable treatment can be provided to postsurgical patients with colorectal cancer who have a high risk of worsening prognosis.

EMBODIMENTS OF THE INVENTION

1. Therapeutic Agent for Colorectal Cancer

Figure 1:
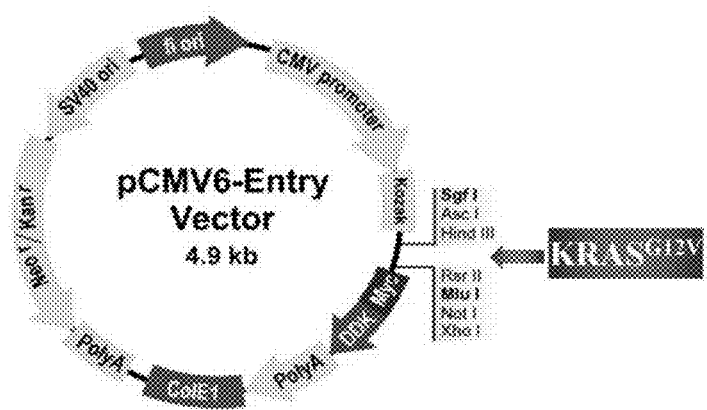
FIG. 1 shows a structure of a vector pCMV6 used in Example 1.

The therapeutic agent for colorectal cancer of the present invention includes either one or both of miR4689 and miR4685-3p as an active ingredient. In the following, the therapeutic agent for colorectal cancer of the present invention will be described in detail.

Active Ingredient (microRNA)

The therapeutic agent for colorectal cancer of the present invention includes either one or both of miR4689 and miR4685-3p as an active ingredient. Although the miR4689 and the miR4685-3p are well-known microRNAs, their antitumor effect is not known. Either one or both of the miR4689 and the miR4685-3p used in the present invention may be a mature miRNA (mature-miRNA), or may be a hairpin-type miRNA precursor (pri-miRNA) or a pre-miRNA that is a partial pri-miRNA cleaved from the pri-miRNA. The pri-miRNA or the pre-miRNA is processed within colorectal cancer cells to become a mature miRNA. Alternatively, either one or both of the miR4689 and the miR4685-3p used in the present invention, together with an RNA molecule having a complementary base sequence, may form a double-stranded precursor. The double strand of the double-stranded precursor breaks within colorectal cancer cells and releases a mature miRNA.

Alternatively, either one or both of the miR4689 and the miR4685-3p used in the present invention may have various ordinary nucleic-acid modifications, as needed, for properties such as resistance to enzymatic degradation. Examples of the modifications include modification in a sugar chain part, such as 2'-O methylation; modification in a base part;

and modification in a phosphoric acid part, such as amination, lower alkyl amination, and acetylation.

The origin of either one or both of the miR4689 and the miR4685-3p used in the present invention may be appropriately selected depending on the type of the target animal. When treating human colorectal cancer, for example, a human miR4689 and/or a human miR4685-3p is used. Specific examples of the base sequence of the human miR4689 include UUGAGGAGACAUGGUGGGGCC (SEQ ID NO: 1). Specific examples of the base sequence of the human miR4685-3p include UCUCCCUUCCUGC-CCUGGCUAG (SEQ ID NO: 2).

In the present invention, either one of miR4689 or miR4685-3p may be used, or both of them may be used in combination. From the viewpoint of further excellent antitumor effect on colorectal cancer cells, miR4689 is preferable.

Target Disease, Dose, Dosage Regimen, and the Like

The therapeutic agent for colorectal cancer of the present invention is applied to a patient with colorectal cancer for the purpose of treating colorectal cancer. Alternatively, the therapeutic agent for colorectal cancer of the present invention may be used as an agent for preventing carcinoma metastasis in a patient with colorectal cancer. Alternatively, the therapeutic agent for colorectal cancer of the present invention may be administered to a patient with colorectal cancer who has undergone colorectal cancer resection, for the purpose of preventing recurrence or metastasis, or may be used as an agent for improving prognosis of a patient after colorectal cancer resection or as an agent for preventing carcinoma metastasis.

The therapeutic agent for colorectal cancer of the present invention exhibits an excellent antitumor effect on KRAS-gene-mutant colorectal cancer that is not effectively treated by administration of an anti-EGFR antibody. Therefore, the therapeutic agent for colorectal cancer of the present invention is suitably used for KRAS-gene-mutant colorectal cancer.

In the present invention, "RAS-gene-mutant colorectal cancer" refers to a colorectal cancer in which a RAS gene in colorectal cancer cell is mutated to code for a RAS having at least one mutated amino acid. Although there is no particular limitation on the site of mutation and the number of mutation in the mutated KRAS gene, a particularly suitable target of the therapeutic agent for colorectal cancer of the present invention is a RAS-gene-mutant colorectal cancer that has amino acid substitution at either one or both of a codon 12 and a codon 13. Specifically speaking, the therapeutic agent for colorectal cancer of the present invention including miR4689 is suitably applied to a RAS-gene-mutant colorectal cancer that has amino acid substitution at either one or both of the codon 12 and the codon 13, and the therapeutic agent for colorectal cancer of the present invention including miR4685-3p is suitably applied to a RAS-gene-mutant colorectal cancer that has amino acid substitution at the codon 13.

The presence of a mutated KRAS gene in a certain colorectal cancer can be determined by extracting genomic DNA from carcinoma cells derived from the colorectal cancer and detecting mutation in the KRAS gene by a known method. There is a commercially available detection kit for detecting the presence or absence of mutation in the codon 12 or 13 in the KRAS gene, and therefore such a commercially available product can be used to determine whether a certain colorectal cancer is a RAS-gene-mutant one.

The method of administering the therapeutic agent for colorectal cancer of the present invention is not particularly limited as long as the therapeutic agent for colorectal cancer of the present invention can be delivered to colorectal cancer in a living organism. Examples of the method include intravascular (intraarterial or intravenous) injection, continuous infusion, subcutaneous administration, topical administration, and intramuscular administration. Among these, intraarterial or intravenous administration is preferable.

The dose of the therapeutic agent for colorectal cancer of the present invention is appropriately determined depending on the severity of the symptom of the patient, the sex and the age of the patient, and the like, and therefore cannot be determined based on general criteria. Examples of the dose include about 1 mg/m$^2$ to about 100 mg/m$^2$ (surface area of the body) per day in terms of the dose of either one or both of the miR4689 and the miR4685-3p.

Production of Preparation

Either one or both of the miR4689 and the miR4685-3p that is contained in the therapeutic agent for colorectal cancer of the present invention is transferred into colorectal cancer cells, regulates signaling downstream of RAS, and induces apoptosis. For easy transfer into colorectal cancer cells, either one or both of the miR4689 and the miR4685-3p is desirably present together with a microRNA-introducing agent within a preparation. The microRNA-introducing agent may be any one of carbonate apatite particles. Lipofectamine, Oligofectamine, RNAiFect, and the like. Among these microRNA-introducing agents, carbonate apatite particles can be made accumulated on colorectal cancer cells within a living organism and efficiently transferred into the colorectal cancer cells. Therefore, a preferable embodiment of the therapeutic agent for colorectal cancer of the present invention is one in which either one or both of the miR4689 and the miR4685-3p is mixed with carbonate apatite particles or is present in the form of complex particles of either one or both of the miR4689 and the miR4685-3p and carbonate apatite particles.

Next, the carbonate apatite particles used as the microRNA-introducing agent in the therapeutic agent for colorectal cancer of the present invention are described.

(Carbonate Apatite Particles)

Carbonate apatite is a compound of formula $Ca_{10-m}X_m(PO_4)_6(CO_3)_{1-n}Y_n$ that has a structure in which the hydroxyl group of hydroxy apatite $(Ca_{10}(PO_4)_6(OH)_2)$ is partially replaced by $CO_3$. In the formula, X is an element capable of partially replacing Ca in the carbonate apatite, examples of which include Sr, Mn, and rare-earth elements. In the formula, m is generally a positive number of 0 to 1, preferably 0 to 0.1, more preferably 0 to 0.01, even more preferably 0 to 0.001. Y is a group or an element capable of partially replacing $CO_3$ in the carbonate apatite, examples of which include OH, F, and Cl. In the formula, n is generally a positive number of 0 to 0.1, preferably 0 to 0.01, more preferably 0 to 0.001, even more preferably 0 to 0.0001.

The average particle size of the carbonate apatite particles used in the present invention is not particularly limited as long as the carbonate apatite particles can be administered into a living organism and transferred into colorectal cancer cells. From the viewpoint of accumulation on colorectal cancer cells within a living organism and efficient transfer into the colorectal cancer cells, the average particle size of the carbonate apatite particles used in the present invention is generally 50 nm or less, preferably from 1 nm to 40 nm, further preferably from 1 nm to 20 nm, and more preferably from 5 nm to 10 nm.

The average particle size of the carbonate apatite is the value measured by observation using a scanning probe microscope. Before the measurement of the particle size with the scanning probe microscope, the site to be measured should be observed with a CCD camera. As a result, when large particles clearly unsuitable for measurement with a scanning probe microscope are observed (for example, particles with diameters of 5 μm or more), such large particles will be removed from the measurement. As used in the present specification, the term "particle size" means the size of independent particles that can be individually identified when measured with a scanning probe microscope. Therefore, when a plurality of particles form an aggregate, such an aggregate should be counted as a single particle.

The carbonate apatite particles can be obtained by a known method. For example, the carbonate apatite particles can be prepared by making calcium ions, phosphate ions, and hydrogencarbonate ions coexist in an aqueous solution. The concentrations of each type of the ions in the aqueous solution are not particularly limited as long as the carbonate apatite particles can be formed, and may be appropriately set taking into account the following.

The concentration of calcium ions in the aqueous solution is generally from 0.1 mM to 1000 mM, preferably from 0.5 mM to 100 mM, and further preferably from 1 mM to 10 mM.

The concentration of phosphate ions in the aqueous solution is generally from 0.1 mM to 1000 mM, preferably from 0.5 mM to 100 mM, and further preferably from 1 mM to 10 mM.

The concentration of hydrogencarbonate ions in the aqueous solution is generally from 1.0 mM to 10000 mM, preferably from 5 mM to 1000 mM, and further preferably from 10 mM to 100 mM.

Sources of calcium ions, phosphate ions, and hydrogencarbonate ions are not particularly limited as long as they can supply the ions to the aqueous solution, and examples thereof include water-soluble salts of these ions. More specifically, $CaCl_2$ may be used as a calcium ion source, $NaH_2PO_4 \cdot 2H_2O$ may be used as a phosphate ion source, and $NaHCO_3$ may be used as a carbonate ion source.

The aqueous solution for preparation of the carbonate apatite particles may contain other components than the respective ion sources and an additional substance, as long as the carbonate apatite particles can be formed. For example, fluoride ions, chloride ions, Sr, Mn, or other species may be added to the aqueous solution so that in the composition, such a species can partially replace Ca or $CO_3$ in carbonate apatite. The added amount of fluoride ions, chloride ions, Sr, or Mn is preferably in a range where there is no significant effect on the pH-solubility of the formed complex particles or the particle size range of the formed complex particles. The base material used in the aqueous solution for preparation of the carbonate apatite particles may be water, or may be various cell culture media or buffers, for example.

In preparation of the carbonate apatite particles used in the present invention, the order in which the respective ion sources and the additional substance are mixed into the aqueous solution is not particularly limited, and the aqueous solution may be prepared in any mixing order as long as desired carbonate apatite particles can be obtained. For example, the aqueous solution can be prepared by a process including preparing a first solution containing calcium ions and the additional substance, separately preparing a second solution containing phosphate ions and hydrogencarbonate ions, and mixing the first and second solutions.

The carbonate apatite particles can be obtained by leaving to itself (incubating), for a certain period of time, the aqueous solution containing each type of the ions with the pH of the aqueous solution adjusted to the range of 6.0 to 9.0. In the process of forming the carbonate apatite particles, the pH of the aqueous solution is from 7.0 to 8.5, for example, preferably from 7.1 to 8.5, further preferably from 7.2 to 8.5, furthermore preferably from 7.3 to 8.5. particularly preferably from 7.4 to 8.5, and most preferably from 7.5 to 8.0.

In the process of forming the carbonate apatite particles, the temperature condition of the aqueous solution is not particularly limited as long as the carbonate apatite particles can be formed, and is generally 10° C. or more, preferably from 25° C. to 80° C., and further preferably from 37° C. to 70° C. or higher.

In the process of forming the carbonate apatite particles, the time to incubate the aqueous solution is not particularly limited as long as the carbonate apatite particles can be formed, and is generally from 1 minute to 24 hours and preferably from 10 minutes to 1 hour. Formation of such particles can be checked by observation with a microscope, for example.

The method for regulating the carbonate apatite particles to an average particle size of 50 nm or less is not particularly limited. Examples of the method include a method of ultrasonic vibration treatment of the carbonate apatite particles formed in the aqueous solution. As used herein, the term "ultrasonic vibration treatment" does not refer to a treatment in which ultrasonic waves are applied to a specimen by bringing the specimen into direct contact with an ultrasonic vibrator of an ultrasonic crusher, a homogenizer, or other means for use in what is called cell-disruption or other procedures, but refers to a treatment using an ultrasonic cleaner having an ultrasonic vibrator and a cleaning tank integrated together generally for use in cleaning precision instruments, test tubes, or other objects. The ultrasonic vibration treatment means a process including placing a liquid (such as water) in the cleaning tank (water tank) of an ultrasonic cleaner, allowing a vessel (such as a plastic tube) to float in the liquid, wherein the vessel contains the carbonate apatite particles, and applying ultrasonic waves to an aqueous solution containing the carbonate apatite particles through the liquid in a similar manner to cleaning precision instruments. This process makes it possible to conveniently and efficiently reduce the size of the carbonate apatite particles to 50 nm or less.

The device that can be used in the ultrasonic vibration treatment is not particularly limited as long as it can apply ultrasonic vibration indirectly to a vessel containing the carbonate apatite particles through a solvent such as water, like the ultrasonic cleaner does. In view of versatility and good handleability, an ultrasonic cleaner having an ultrasonic vibrator and a thermostatic tank is preferably used.

The conditions under which the ultrasonic vibration treatment is performed are not particularly limited as long as the particle size can be regulated to the predetermined range. For example, the temperature of the water tank may be appropriately selected from temperatures ranging from 5° C. to 45° C., preferably from 10° C. to 35° C., and further preferably from 20° C. to 30° C. The high-frequency power in the ultrasonic vibration treatment may be appropriately set in the range from 10 W to 500 W, for example, preferably from 20 W to 400 W, further preferably from 30 W to 300 W, and more preferably from 40 W to 100 W. The oscillating frequency is generally from 10 Hz to 60 Hz, preferably from 20 Hz to 50 Hz, and further preferably from 30 Hz to 40 Hz. The time period of the ultrasonic vibration treatment is within the range from 30 seconds to 30 minutes, for example, preferably within the range from 1 minute to 20 minutes, and further preferably within the range from 3 minutes to 10 minutes.

In the process of performing the ultrasonic vibration treatment, the type of vessel to contain the carbonate apatite particles is not limited as long as the size of the particles can be reduced to the predetermined range of particle size. Such a vessel may be appropriately selected depending on the volume of the aqueous solution or the intended use of the aqueous solution. For example, a plastic tube with a capacity of 1 ml to 1000 ml may be used.

The ultrasonic vibration treatment is preferably performed in the presence of albumin (in other words, after albumin is added to the aqueous solution containing the carbonate apatite particles). This is because when the ultrasonic vibration treatment is performed in an environment where the carbonate apatite particles coexist with albumin, carbonate apatite nanoparticles with smaller sizes can be obtained, and reaggregation of the particles can also be suppressed. The concentration of albumin in the aqueous solution containing the carbonate apatite particles is not particularly limited as long as the effects of particle size reduction and/or of reaggregation suppression can be obtained. Albumin can be added in an amount from about 0.1 mg/ml to about 500 mg/ml, for example, preferably from about 1 mg/ml to about 100 mg/ml, and further preferably from about 1 mg/ml to about 10 mg/ml.

(Complex Particles of Either One or Both of miR4689 and miR4685-3p and Carbonate Apatite Particles)

In a preferable embodiment of the therapeutic agent for colorectal cancer of the present invention, the complex particles of either one or both of the miR4689 and the miR4685-3p and the carbonate apatite particles are used. This form of either one or both of the miR4689 and the miR4685-3p as the complex with the carbonate apatite particles enables either one or both of the miR4689 and the miR4685-3p to be efficiently accumulated on colorectal cancer cells within a living organism by the action of carbonate apatite and be introduced into the colorectal cancer cells. In addition, after introduction into the cells, either one or both of the miR4689 and the miR4685-3p can be released from the carbonate apatite particles within the cells, and, as a result, an antitumor effect of either one or both of the miR4689 and the miR4685-3p can be efficiently exhibited.

In the present invention, the complex particles of either one or both of the miR4689 and the miR4685-3p and the carbonate apatite particles refer to the state in which either one or both of the miR4689 and the miR4685-3p is adsorbed and supported on the carbonate apatite particles via an ionic bond, a hydrogen bond, and the like. The method of forming the complex particles of either one or both of the miR4689 and the miR4685-3p and the carbonate apatite particles is not particularly limited. Examples of the method include a method of making either one or both of the miR4689 and the miR4685-3p and the carbonate apatite particles coexist in an aqueous solution; and a method of, in an aqueous solution that is used for preparation of the carbonate apatite particles, making either one or both of the miR4689 and the miR4685-3p coexist with calcium ions, phosphate ions, and hydrogencarbonate ions, so as to simultaneously perform formation of the carbonate apatite particles and formation of the complex of either one or both of the miR4689 and the miR4685-3p and the carbonate apatite particles.

Regarding formation of the complex particles of either one or both of the miR4689 and the miR4685-3p and the carbonate apatite particles, when formation of the carbonate apatite particles and formation of the complex of either one or both of the miR4689 and the miR4685-3p and the carbonate apatite particles are simultaneously performed, either one or both of the miR4689 and the miR4685-3p may be added to the aqueous solution that is used for preparation of carbonate apatite, in an amount from 0.1 nM to 1000 nM, for example, preferably from 0.5 nM to 500 nM, and further preferably from 1 nM to 200 nM.

In the complex particles of either one or both of the miR4689 and the miR4685-3p and the carbonate apatite particles, the ratio of either one or both of the miR4689 and the miR4685-3p to the carbonate apatite particles is not particularly limited, and may be appropriately determined, for example, depending on the dose of either one or both of the miR4689 and the miR4685-3p. In the case of forming a complex that includes either one or both of the miR4689 and the miR4685-3p in an amount of 2 mg and the carbonate apatite particles, for example, 5 mg of either one or both of the miR4689 and the miR4685-3p may be added to 2.5 L of the aqueous solution that is used for preparation of the carbonate apatite particles as described above, so as to simultaneously perform formation of the carbonate apatite particles and formation of the complex of either one or both of the miR4689 and the miR4685-3p and the carbonate apatite particles.

When either one or both of the miR4689 and the miR4685-3p used as the therapeutic agent for colorectal cancer of the present invention is in the form of complex with the carbonate apatite particles, either one or both of the miR4689 and the miR4685-3p is in the state of dispersion in a solvent suitable for administration to a living organism. As described above, the carbonate apatite particles are obtained by dissolving various substances, which are to serve as ion sources, in a solvent such as water, a medium, or a buffer. The resulting solution in which the carbonate apatite particles are thus dispersed is not necessarily suitable for administration to a living organism (intravascular administration) from the viewpoints of osmotic pressure, buffering capacity, sterility, and the like. Therefore, the solvent in which the carbonate apatite particles are dispersed is replaced by a solvent suitable for administration to a living organism (such as physiological saline). For this replacement, a process of separating and recovering the carbonate apatite particles from the solvent by centrifugation and replacing the solvent is generally required. By this process, however, the carbonate apatite particles become aggregated to each other to form large particles, which are, again, not suitable for administration to a living organism. To solve this problem, the aggregated carbonate apatite particles are added to a solvent suitable for administration to a living organism, and then the ultrasonic vibration treatment described above is performed. As a result, the particle size of the complex particles of either one or both of the miR4689 and the miR4685-3p and the carbonate apatite particles dispersed in the solvent suitable for administration to a living organism becomes an appropriate particle size (preferably, an average particle size of 50 nm or less).

When either one or both of the miR4689 and the miR4685-3p used as the therapeutic agent for colorectal cancer of the present invention is in the form of complex with the carbonate apatite particles, it is desirable that administration of the therapeutic agent for colorectal cancer of the present invention is performed immediately after the complex particles of either one or both of the miR4689 and the miR4685-3p and the carbonate apatite particles are dispersed by the ultrasonic vibration treatment and before the resulting microparticles become reaggregate. For example, administration is preferably performed within 1 minute, preferably 30 seconds, after the ultrasonic vibration treatment. Alternatively, when albumin is added as described above for suppressing aggregation of the carbonate apatite particles, administration can be performed several minutes to several dozen minutes after the ultrasonic vibration treatment.

Additional Anticancer Agents

The therapeutic agent for colorectal cancer of the present invention may be present together with an additional anticancer agent in the preparation or may be co-administered with an additional anticancer agent, as long as the effects of the present invention are not impaired. The anticancer agent is not particularly limited, and examples thereof include alkylating agents such as cyclophosphamide hydrate, ifosfamide, thiotepa, busulfan, melphalan, nimustine hydrochloride, ranimustine, dacarbazine, and temozolomide; antimetabolites such as methotrexate, pemetrexed sodium hydrate, fluorouracil, doxifluridine. capecitabine, tegafur, cytarabine, gemcitabine hydrochloride, fludarabine phosphate, nelarabine, cladribine, and levofolinate calcium; antibiotics such as doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin C, actinomycin D, bleomycin hydrochloride, peplomycin hydrochloride, zinostatin stimalamer, and calicheamicin, microtubule inhibitors such as vincristine sulfate, vinblastine sulfate, vindesine sulfate, and paclitaxel; aromatase inhibitors such as anastrozole, exemestane, letrozole, and fadrozole hydrochloride hydrate; platinum agents such as cisplatin, carboplatin, nedaplatin, and oxaliplatin; and topoisomerase inhibitors such as irinotecan hydrochloride hydrate, nogitecan hydrochloride. etoposide, and sobuzoxane, adrenocorticosteroids such as prednisolone and dexamethasone, thalidomide and a derivative thereof such as lenalidomide, and a protease inhibitor such as bortezomib. These anticancer agents may be used alone or in combination of two or more.

2. Method of Predicting Prognosis of Patient with Colorectal Cancer

Example 16 below shows that patients with colorectal cancer who had colorectal cancer with decreased expression levels of miR4689 had a tendency that the prognosis worsened after colorectal cancer resection, clearly indicating that miR4689 can be used as a marker for predicting prognosis of patients with colorectal cancer. Thus, the present invention further provides a method of predicting prognosis of a patient with colorectal cancer, the method including detecting expression level of miR4689 in colorectal cancer cells from a patient with colorectal cancer. In this method of prediction, decreased expression level of miR4689 give a prediction that the risk of postsurgical recurrence and metastasis is high and the prognosis is likely to become worse.

Specifically, the prognosis prediction based on expression level of miR4689 can be performed by the following steps: measuring, in advance, expression levels of miR4689 in colorectal cancer cells from patients with Stage 0 to Stage 111 colorectal cancer who have undergone surgery (population); calculating the median in the population; and, when colorectal cancer cells from a patient with colorectal cancer have expression level of miR4689 that is lower than the median, making a prediction that the risk of postsurgical recurrence and metastasis is high and the prognosis is likely to become worse.

Alternatively, the prognosis prediction based on the expression level of miR4689 can be performed, for example, by the following steps: (i) calculating, in advance, the average level of miR4689 in patients with colorectal cancer who have excellent prognoses; and, when colorectal cancer cells from a patient with colorectal cancer have expression level of miR4689 that is lower than the average level, making a prediction that the risk of postsurgical recurrence and metastasis is high and the prognosis is likely to become worse; (ii) calculating, in advance, the average level of miR4689 in patients with colorectal cancer who have poor prognoses; and, when colorectal cancer cells from a patient with colorectal cancer have expression level of miR4689 that is substantially the same as the average value, making a prediction that the risk of postsurgical recurrence and metastasis is high and the prognosis is likely to become worse, or (iii) measuring, respectively, the average level of miR4689 in patients with colorectal cancer who have excellent prognoses (the average value for an excellent-prognosis group) and the average level of miR4689 in patients with colorectal cancer who have poor prognoses (the average value for a poor-prognosis group); calculating, in advance, the average value (the boundary value) of the average level for the excellent-prognosis group and the average level for the poor-prognosis group; and, then, when colorectal cancer cells from a patient with colorectal cancer have expression level of miR4689 that is lower than the boundary value, making a prediction that the risk of postsurgical recurrence and metastasis is high and the prognosis is likely to become worse.

Measurement of the expression level in colorectal cancer cells can be performed by a conventionally known method. For example, the measurement may be performed by separating colorectal cancer cells from colorectal carcinoma tissue of patients with colorectal cancer, obtaining an RNA specimen from the colorectal cancer cells by the guanidine-cesium chloride ultracentrifugation method, the acid guanidinium-phenol-chloroform (AGPC) method, or the like, and measuring expression level of miR4689. The method of measuring the expression is not particularly limited. and examples thereof include the microarray method, RT-PCR. real-time RT-PCR, and Northern blotting.

EXAMPLES

Next, the present invention will be described in detail based on examples and the like. The scope of the present invention, however, is not limited to them. In the tests below, informed consent was obtained from all the patients who provided specimens, according to the guideline approved by respective institution. The tests were conducted under the supervision of the ethics committee of Osaka University Hospital.

Example 1: Measurement of Changes in Expression Levels of microRNAs in Cells Having Mutated KRAS Gene Introduced Thereinto In order to measure changes in expression levels of microRNAs in cells having a mutated KRAS gene introduced thereinto, the following test was conducted.

First, a mutated KRAS gene (G12V; SEQ ID NO: 3) was inserted into the SgfI-MluI site of a pCMV6 Empty Vecter (FIG. 1) to prepare a G12Vkras mt plasmid for use. Then, the resulting G12Vkras mt plasmid was introduced into a normal human cell [HEK293 (human embryonic kidney cell), MRC5 (human embryonic lung cell)] with the use of Lipofectamine 2000, and, as a result, a mutated-KRAS-gene-introduced cell was prepared. As a control, a pCMV6 Empty Vecter into which no mutated KRAS gene (G12V)

was inserted was introduced into normal human cells, and, as a result, control cells was prepared. The resulting mutated-KRAS-gene-introduced cells and the resulting control cells were subjected to measurement of their expression patterns of microRNAs with the use of a miRNA microarray (3D-GENE, manufactured by Toray Industries, Inc.). In a 6-well dish (2.5 ml), 4 µg of the G12Vkras mt plasmid and 10 µg of Lipofectamine were placed, and, after 48 hours, the cells were collected.

Figure 2:
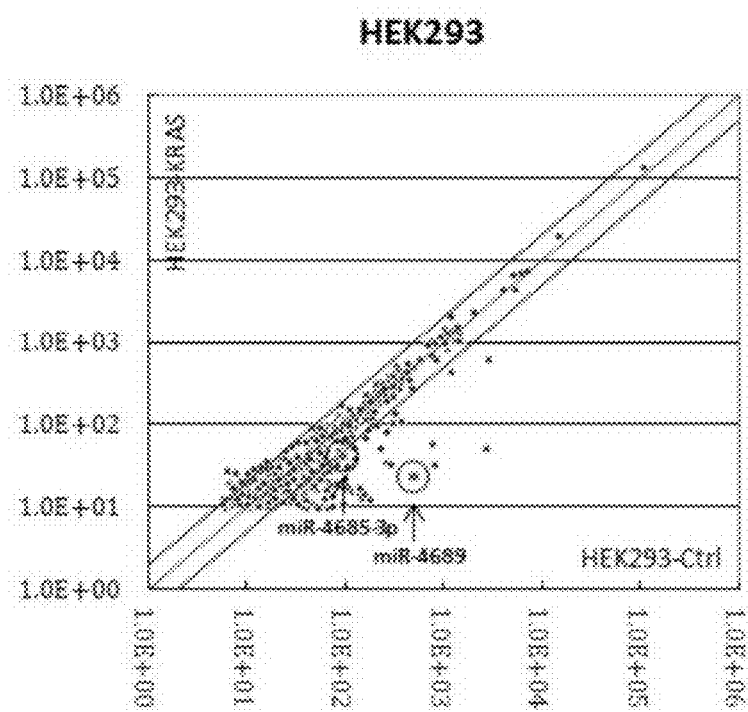
FIG. 2 shows measurement results of Example 1, showing changes in expression levels of microRNAs in an HEK293 cell into which a mutated KRAS gene (G12V) was introduced.
Figure 3:
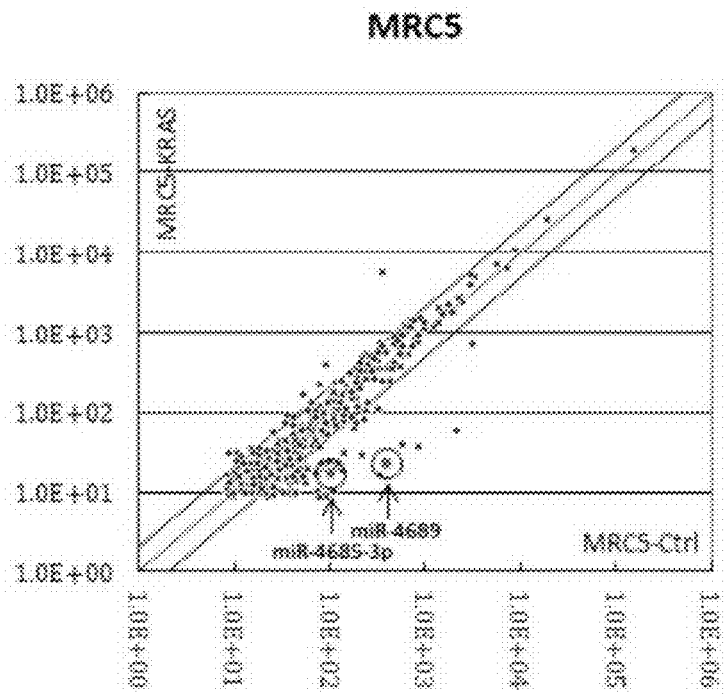
FIG. 3 shows measurement results of Example 1, showing changes in expression levels of microRNAs in an MRC5 cell into which a mutated KRAS gene (G12V) was introduced.

The results with HEK293 cells are shown in FIG. 2, and the results with MRC5 cells are shown in FIG. 3. These results showed a tendency that, in either of the HEK293 and MRC5 cells, many microRNAs experienced decreases in their expression levels due to introduction of the mutated KRAS gene.

Figure 4:
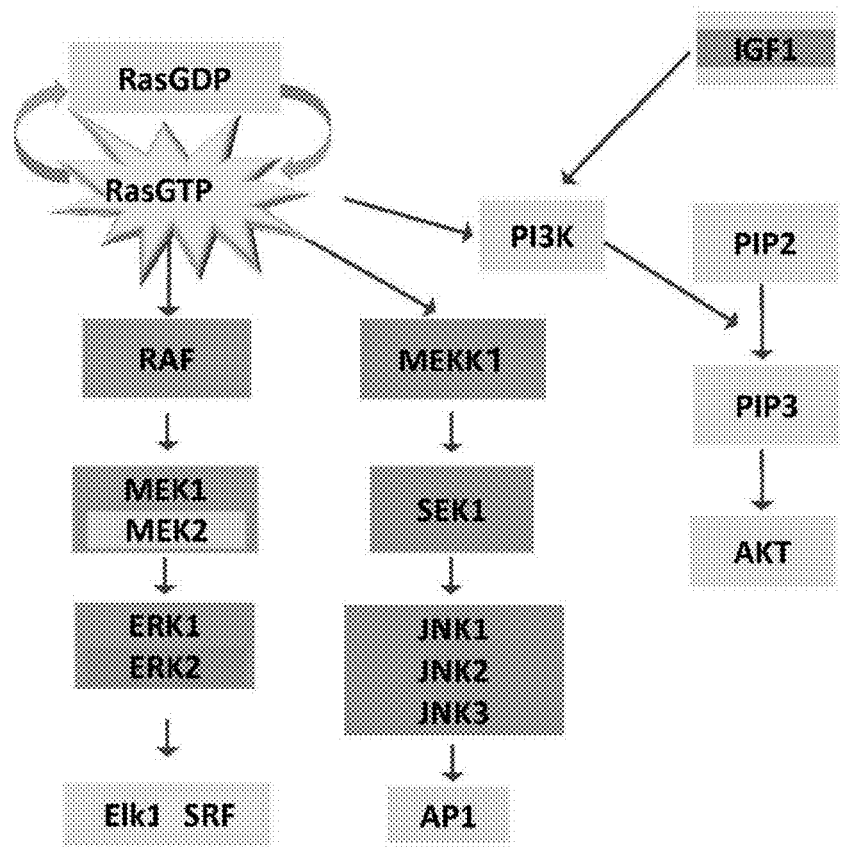
FIG. 4 is a schematic view of signal pathways downstream of RAS.

Separately, microRNAs targeting any molecule in signal pathways downstream of RAS (FIG. 4) were searched in the Targetscan (http://www.targetscan.org/). Among the microRNAs, ones that were found in the measurement above to have experienced changes in their expression levels were selected. miR4685-3p, miR4689, and miR296-5p are each known as a microRNA that targets MEK2, ERK, and SRF, respectively, and these microRNAs were found to have experienced decreases in their expression levels due to introduction of the mutated KRAS gene (Table 1).

TABLE 1

| | Changes in expression levels due to introduction of mutated KRAS gene (fold-change) | |
|---|---|---|
| | HEK293 cells | MRC5 cells |
| miR4685-3p | −1.33 | −2.53 |
| miR4689 | −20.0 | −16.7 |
| miR296-5p | −14.3 | −14.3 |

Regarding the tests in both of the HEK293 and MRC5 cells, among the microRNAs that experienced decreases in their expression levels due to introduction of the mutated KRAS gene to −4 times (¼) or smaller expression levels in the control, 14 microRNAs were selected in order of decreasing decrement in their expression levels and shown in Table 2. As shown in Table 2, many of the microRNAs that had a great decrement in their expression levels were microRNAs in the 3000s and the 4000s the functions of which had not yet been reported.

TABLE 2

| | Changes in expression levels due to introduction of mutated KRAS gene (fold-change) | |
|---|---|---|
| | HEK293 cells | MRC5 cells |
| miR-4442 | −50.0 | −13.3 |
| miR-4270 | −25.0 | −25.0 |
| miR-4689 | −20.0 | −16.7 |
| miR-296-5p | −14.3 | −14.3 |
| miR-3619-3p | −9.1 | −20.1 |
| miR-4731-3p | −10.0 | −10.0 |
| miR-1249 | −8.4 | −5.5 |
| miR-3675-3p | −11.2 | −6.3 |
| miR-3679-3p | −8.1 | −7.4 |
| miR-371-5p | −5.6 | −4.2 |
| miR-3162-5p | −5.6 | −7.3 |
| miR-4675 | −6.5 | −5.0 |
| miR-4716-5p | −4.4 | −4.7 |
| miR-4723-5p | −4.7 | −4.4 |

Figure 5:
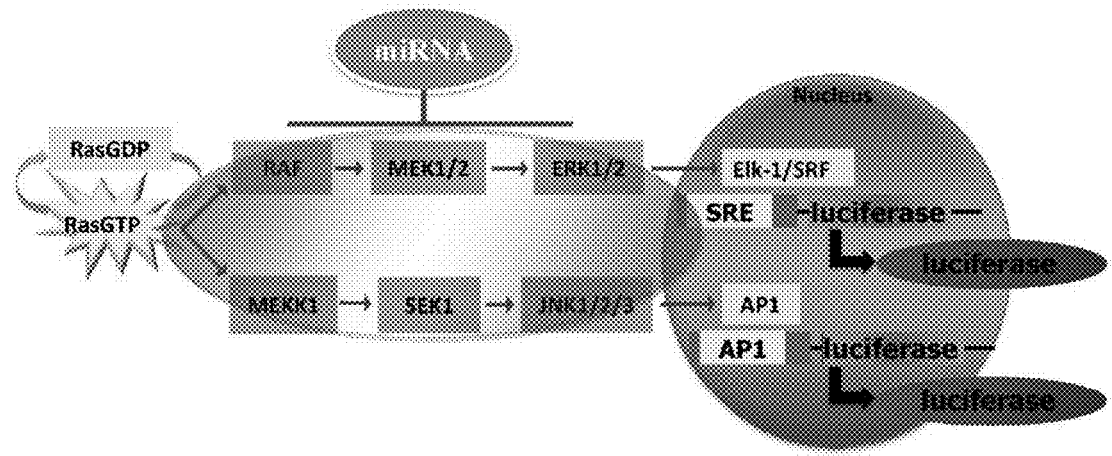
FIG. 5 is a schematic view of signal pathways downstream of RAS.

Example 2: Measurement of RAF-MEK-ERK-Elk-1/SRF Activity and MEKK1-SEK1-JNK1/2/3-AP1 Activity in HEK293 Cells Having Mutated KRAS Gene Introduced Thereinto It is known that RAF-MEK-ERK-Elk-1/SRF activity, which is a signal downstream of RAS, can be measured by measuring SRE reporter activity and that MEKK1-SEK1-JNK1/2/3-AP1 activity, which is also a signal downstream of RAS. can be measured by measuring AP1 reporter activity (FIG. 5). In this study, SRE luciferase reporter vector (pGL4.33[luc2P/SRE/Hygro] Vector, catalogue No. E1340) or AP1 luciferase reporter vector (pGL4.44[luc2P/AP1 RE/Hygro] Vector, catalogue No. E4111) having SRE response element or AP1 response element incorporated thereinto upstream of the luciferase gene was transfected into HEK293 cells along with the mutated KRAS gene. The influence, in the resulting cells, of the microRNAs selected in Example 1 on RAF-MEK-ERK-Elk-1/SRF activity and MEKK1-SEK1-JNK1/2/3-AP1 activity was evaluated.

Specific procedure was as follows. HEK293 cells were seeded at 1×10⁴ cells/ml in D-MEM medium (containing FBS in an amount of 10% by volume) within a 96-well plate, followed by overnight culture at 37° C. Subsequently, 100 ng/well of SRE luciferase reporter vector, 100 ng/well of the G12Vkras mt plasmid prepared in Example 1, 5 pmol/well of each microRNA, and 0.75 l/well of Lipofectamine 2000 were used for further culturing for 6 hours at 37° C. for transfection. Then, the medium was exchanged to D-MEM medium (containing FBS in an amount of 10% by volume), followed by culturing for another 18 hours. The expression level of luciferase was measured (24 hours after transfection). Among the microRNAs selected in Example 1, miR4270, miR4689, miR4685-3p, miR296-5p, miR3619-3p, miR4731-3p, and miR4442 were used in this test. In addition to these microRNAs, a control microRNA (NCmiR, SEQ ID NO: 4) was also tested under the same conditions. Earlier in this study, transfection of HEK293 cells with the EGF gene or the mutated KRAS gene was performed and increases in the expression level of luciferase ware observed, so that normal functioning of the RAF-MEK-ERK-Elk-1/SRF pathway and the MEKK1-SEK1-JNK1/2/3-AP1 pathway in HEK293 cells was confirmed (FIGS. 6 and 7).

Figure 6:
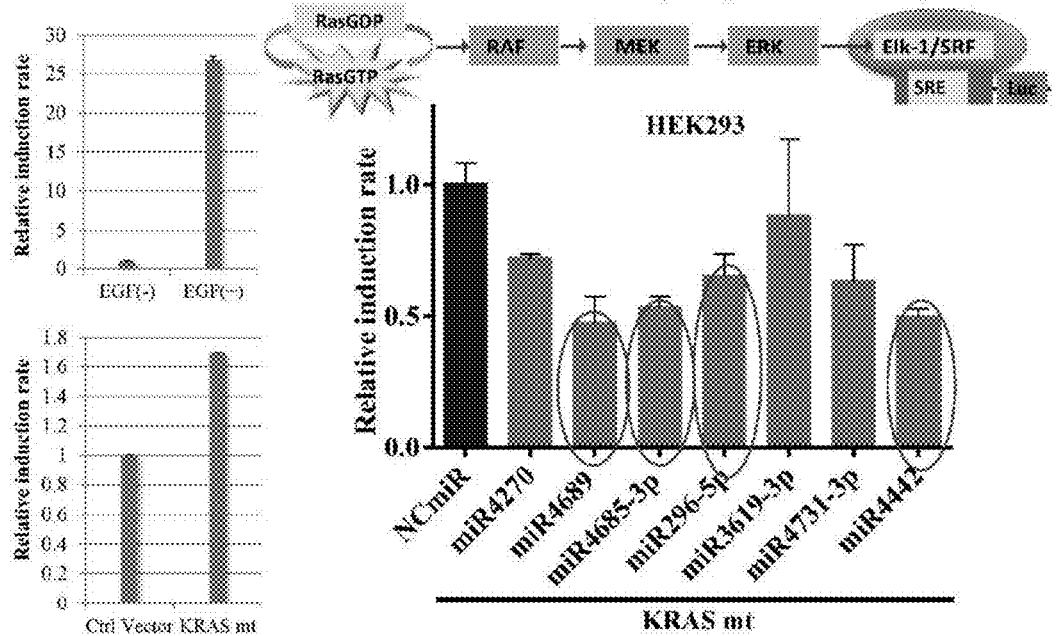
FIG. 6 shows results of Example 2, evaluating the influence of microRNAs on SRE reporter activity in HEK293 cells into which SRE luciferase reporter vector and a mutated KRAS gene were introduced.
Figure 7:
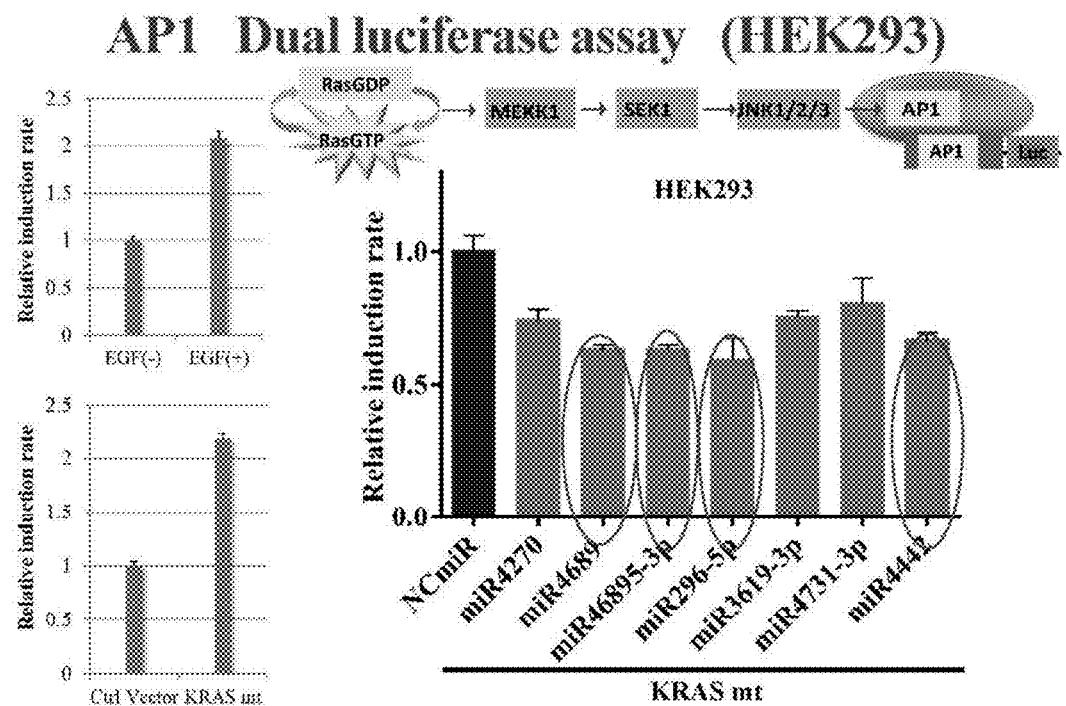
FIG. 7 shows results of Example 2, evaluating the influence of microRNAs on AP1 reporter activity or AP1 reporter activity in HEK293 cells into which AP1 luciferase reporter vector and a mutated KRAS gene were introduced.

The results of measurement of SRE reporter activity after introduction of each microRNA are shown in FIG. 6. The results of measurement of AP1 reporter activity after introduction of each microRNA are shown in FIG. 7. These results indicated that miR4685-3p and miR4689 had strong action of decreasing signaling activity in both RAF-MEK-ERK-Elk-1/SRF and MEKK1-SEK1-JNK1/2/3-AP1 pathways.

Example 3: Evaluation of Influence of miR4685-3p and miR4689 on Regulation of Signaling Downstream of RAS in Colorectal Cancer Cells Having Mutated KRAS Gene, and on Cell Proliferation In order to evaluate whether miR4685-3p and miR4689 can actually regulate signaling downstream of RAS in KRAS mutant colorectal cancer cells and suppress the cell proliferation, the following test was conducted.

DLD1 cells (human colorectal cancer cells, having G13D mutation in the KRAS gene), HCT116 cells (human colorectal cancer cells, having G13D mutation in the KRAS gene), and SW480 cells (human colorectal cancer cells, having G12V mutation in the KRAS gene) were used as carcinoma cells. First, each carcinoma cells were seeded at 1×10⁴ cells/ml in D-MEM medium (containing FBS in an amount of 10% by volume) within a 96-well plate, followed by overnight culture at 37° C. Subsequently, 5 pmol/well of each microRNA, 0.5 µl/well of Lipofectamine 2000, and 100 ng/well of SRE luciferase reporter vector (pGL4.33 [luc2P/SRE/Hygro] Vector, catalogue No. E1340) or AP1 luciferase reporter vector (pGL4.44[luc2P/AP1 RE/Hygro] Vector, catalogue No. E4111) having SRE response element or AP1 response element incorporated thereinto upstream of the luciferase gene were added thereto, followed by culturing for another 6 hours at 37° C. for transfection. Then, the medium was exchanged to D-MEM medium (containing FBS in an amount of 10% by volume), followed by culturing. The expression level of luciferase was measured 24 hours after transfection. The cells were counted 24, 48, and 72 hours after transfection. As controls in this test, a case in which no microRNA was introduced (Parent) and a case in which a control microRNA (SEQ ID NO: 4) was used instead of the microRNAs (miRNC) were also tested under the same conditions.

Figure 8:
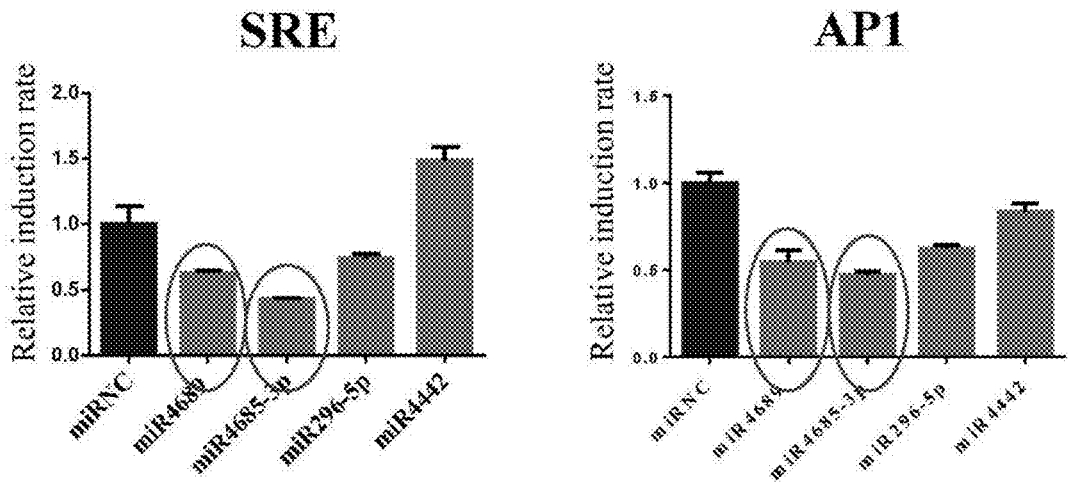
FIG. 8 shows results of Example 3, evaluating the influence of microRNAs on SRE or AP1 reporter activity in DLD1 cells into which SRE luciferase reporter vector or AP1 luciferase reporter vector was introduced.
Figure 9:
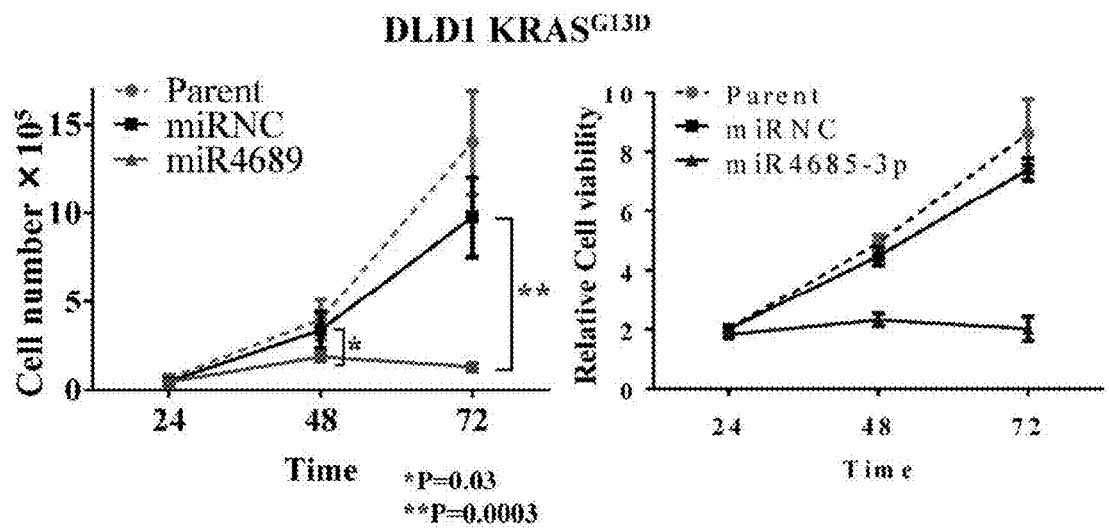
FIG. 9 shows results of Example 3, evaluating the influence of microRNAs on proliferation of DLD1 cells.
Figure 10:
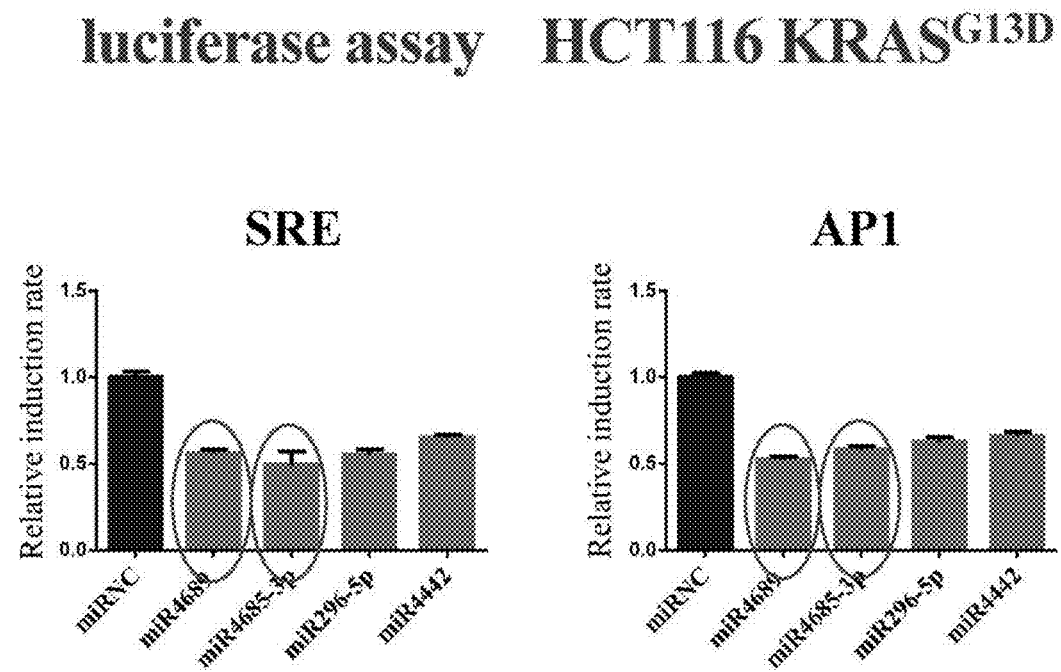
FIG. 10 shows results of Example 3, evaluating the influence of microRNAs on SRE or AP1 reporter activity in HCT116 cells into which SRE luciferase reporter vector or AP1 luciferase reporter vector was introduced.
Figure 11:
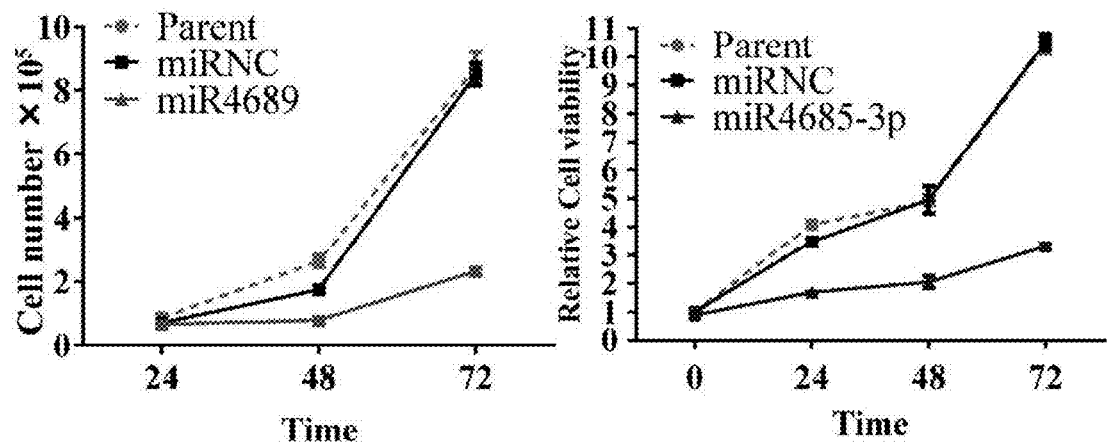
FIG. 11 shows results of Example 3. evaluating the influence of microRNAs on proliferation of HCT116 cells.
Figure 12:
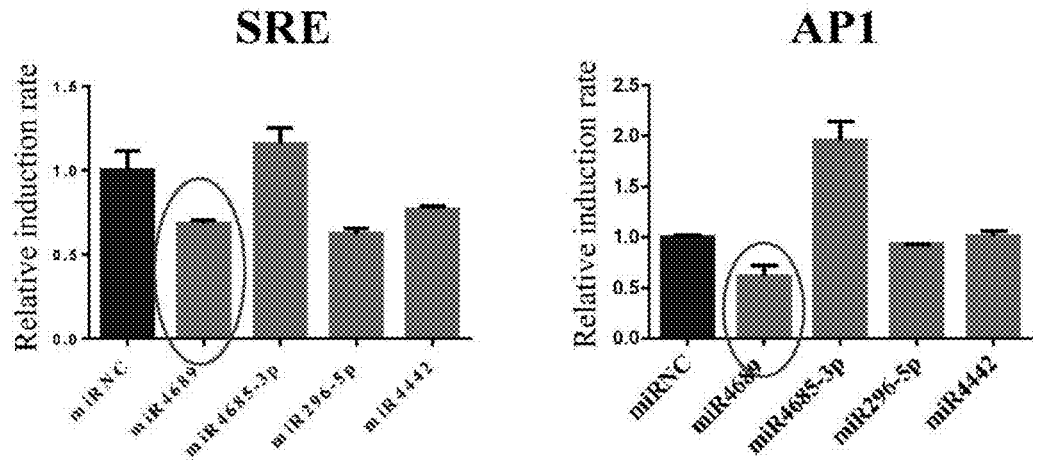
FIG. 12 shows results of Example 3, evaluating the influence of microRNAs on AP1 reporter activity in SW480 cells into which SRE luciferase reporter vector or AP1 luciferase reporter vector was introduced.
Figure 13:
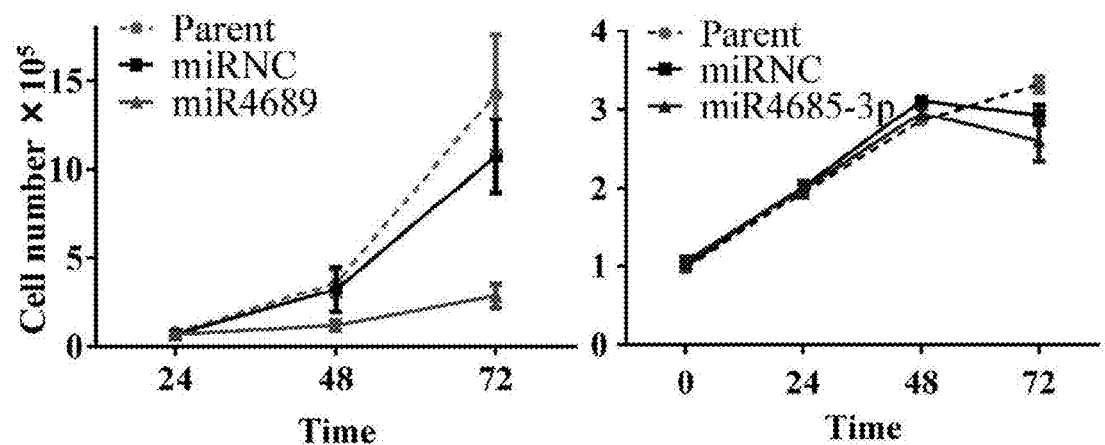
FIG. 13 shows results of Example 3, evaluating the influence of microRNAs on proliferation of SW480 cells.

The results of measurement of SRE reporter activity and AP1 reporter activity in DLD1 cells are shown in FIG. 8, and the time-course results of cell counting are shown in FIG. 9. The results of measurement of SRE reporter activity and AP1 reporter activity in HCT116 cells are shown in FIG. 10, and the time-course results of cell counting are shown in FIG. 11. The results of measurement of SRE reporter activity and AP1 reporter activity in SW480 cells are shown in FIG. 12, and the time-course results of cell counting are shown in FIG. 13. These results showed that miR4685-3p had action of decreasing signaling downstream of RAS in DLD1 and HCT116 cells, indicating that miR4685-3p was capable of suppressing proliferation of these cells. It was also shown that miR4689 had action of decreasing signaling downstream of RAS in all of DLD1, HCT116, and SW480 cells, indicating that miR4689 was capable of effectively suppressing proliferation of these cells.

Example 4: Evaluation of Antitumor Effect of miR4689 on Colorectal Cancer Cells Having Mutated KRAS Gene The test results above showed that miR4689 had action of regulating signaling downstream of RAS in colorectal cancer cells having a mutated KRAS gene and of suppressing proliferation of the cells. In this test, a suppressive effect of miR4689 on proliferation of colorectal cancer cells (DLD1, HCT116, SW480 cells) having a mutated KRAS gene was compared to the same effect of siRNAs (siMEK1/2) the antitumor effect of which was already known.

Specific procedure was as follows. In D-MEM medium (containing FBS in an amount of 10% by volume) within a 24-well plate, 2.5×10⁴ cells of each type were seeded, followed by overnight culture at 37° C. Subsequently, the microRNA or the siRNA was added thereto to achieve a concentration of 50 nM, followed by culturing with 1.0 µl/well of Lipofectamine IMAX for 24 hours at 37° C. for transfection. Then, the medium was exchanged to D-MEM medium (containing FBS in an amount of 10% by volume), followed by culturing. The cells were counted 24, 48, and 72 hours after transfection. As controls in this test, a case in which no microRNA was introduced (Parent) and a case in which a control microRNA (SEQ ID NO: 4) was used instead of the microRNA (miRNC) were also tested under the same conditions.

Figure 14:
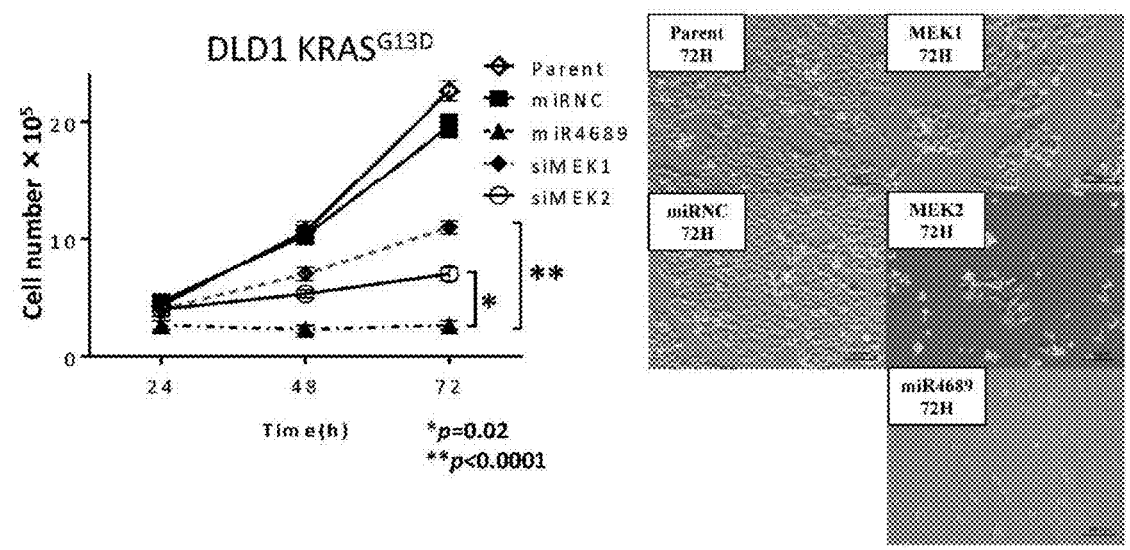
FIG. 14 shows results of Example 4, evaluating the influence of miR4689 and siRNAs on proliferation of DLD1 cells, in which the antitumor effect of the siRNA was known.
Figure 15:
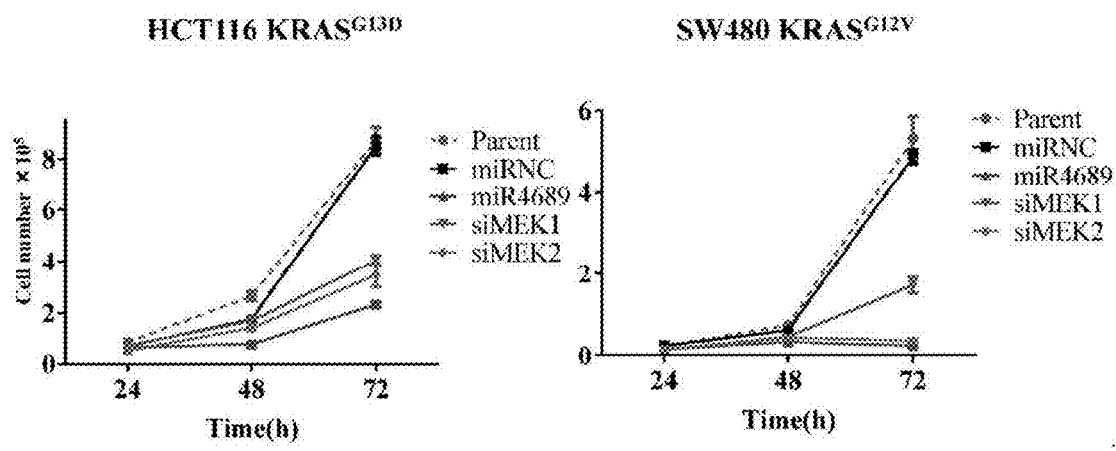
FIG. 15 shows results of Example 4, evaluating the influence of miR4689 and siRNAs on proliferation of HCT116 cells and SW480 cells, in which the antitumor effect of the siRNA was known.

FIG. 14 shows the results regarding DLD1 cells, namely, the time-course results of cell counting and the result of observation of the cell state after 72 hours of culturing. FIG. 15 shows the time-course results of cell counting regarding HCT116 and SW480 cells. These results clearly indicated that miR4689, compared to siMEK1/2, had strong action of suppressing proliferation of colorectal cancer cells having a mutated KRAS gene.

Example 5: Evaluation of Influence of miR4689 on Signal Molecules Downstream of RAS, Expression Levels of Apoptotic Markers, and Induction of Apoptosis in Colorectal Cancer Cells The test results above clearly indicated that miR4689 had action of suppressing proliferation of colorectal cancer cells having a mutated KRAS gene. In this test, in order to clearly understand the action of miR4689, colorectal cancer cells having miR4689 administered thereto was subjected to Western blotting and to measurement of expression levels of signaling molecules downstream of RAS and apoptotic markers.

Specific procedure was as follows. In D-MEM medium (containing FBS in an amount of 10% by volume) within a 6-well plate, 2×10⁵ DLD1 cells were seeded, followed by overnight culture at 37° C. Subsequently, microR was added thereto to achieve a concentration of 50 nM, followed by culturing with 5 µl/well of Lipofectamine IMAX at 37° C. for transfection. Then, the medium was exchanged to D-MEM medium (containing FBS in an amount of 10% by volume), followed by culturing. Western blotting was performed 24, 48, and 72 hours after transfection, and the expression amounts of signaling molecules downstream of RAS and apoptotic marker molecules were measured. In addition, 48 hours after transfection, measurement of expression levels of microRNA and detection of apoptosis by the TUNEL (TdT-mediated dUTP nick end labeling) method with a commercially available kit were also performed. Measurement of microRNA expression levels was performed by RNA extraction with an miReasy kit, reverse transcription with a TaqMan MicroRNA RT Kit (Applied Biosystems, Foster City, Calif.). and real-time quantitative PCR with TaqMan MicroRNA Assays (Applied Biosystems) and 7500HT Sequence Detection System (Applied Biosystems). As controls in this test, a case in which no microRNA was introduced (Parent) and a case in which a control microRNA (SEQ ID NO: 4) was used instead of the microRNA (miRNC) were also tested under the same conditions.

Figure 16:
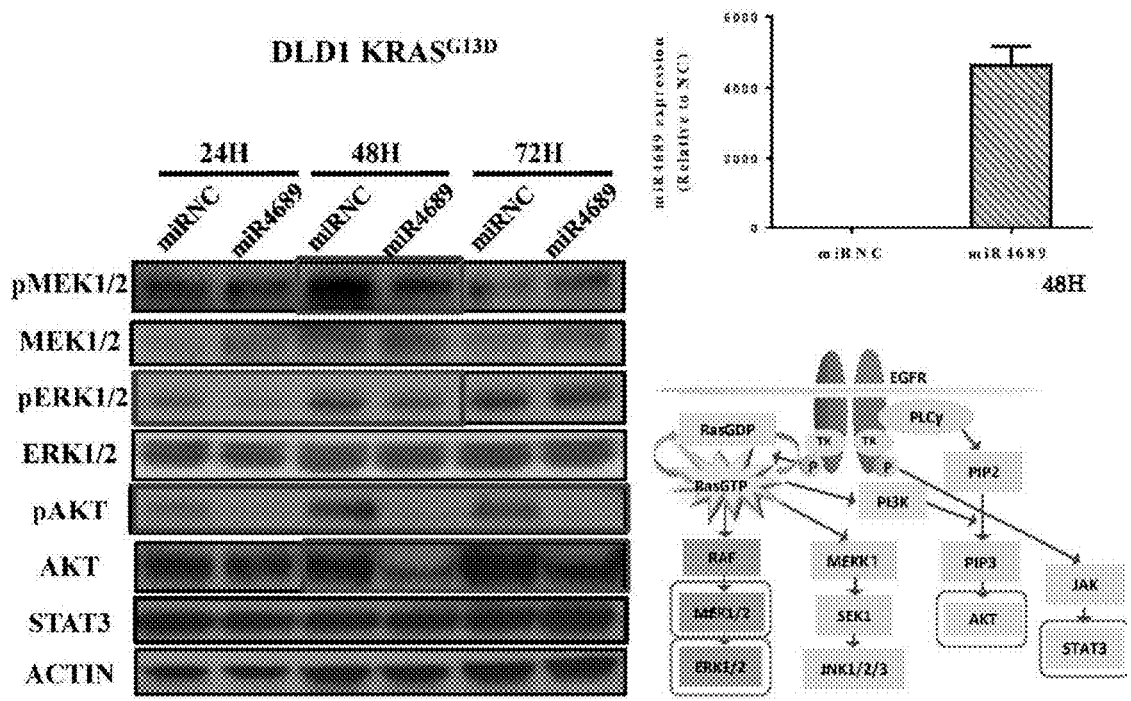
FIG. 16 shows measurement results of Example 5, showing expression levels of signaling molecules downstream of RAS in DLD1 cells into which miR4689 was introduced.
Figure 17:
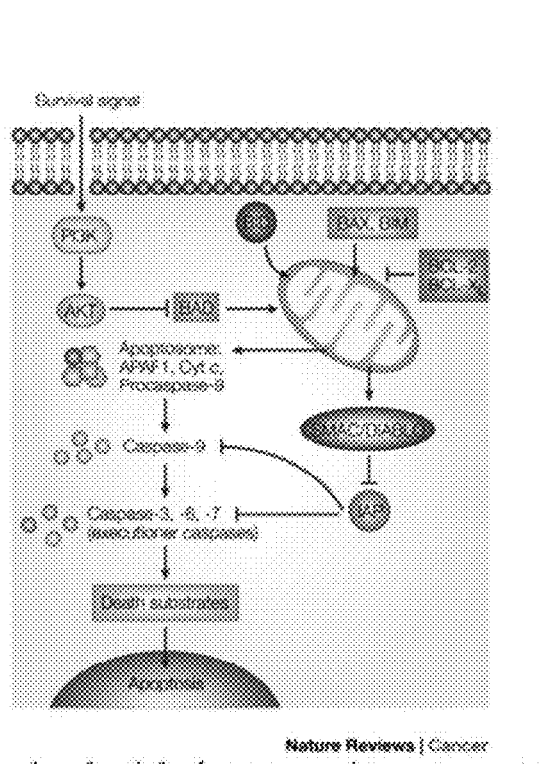
FIG. 17 shows measurement results of Example 5, showing expression levels of apoptotic markers in DLD1 cells into which miR4689 was introduced.
Figure 17:
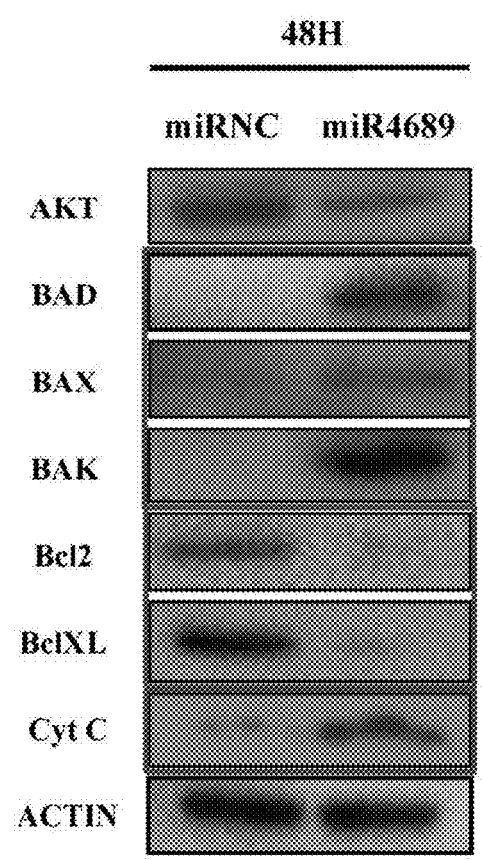
Figure 18:
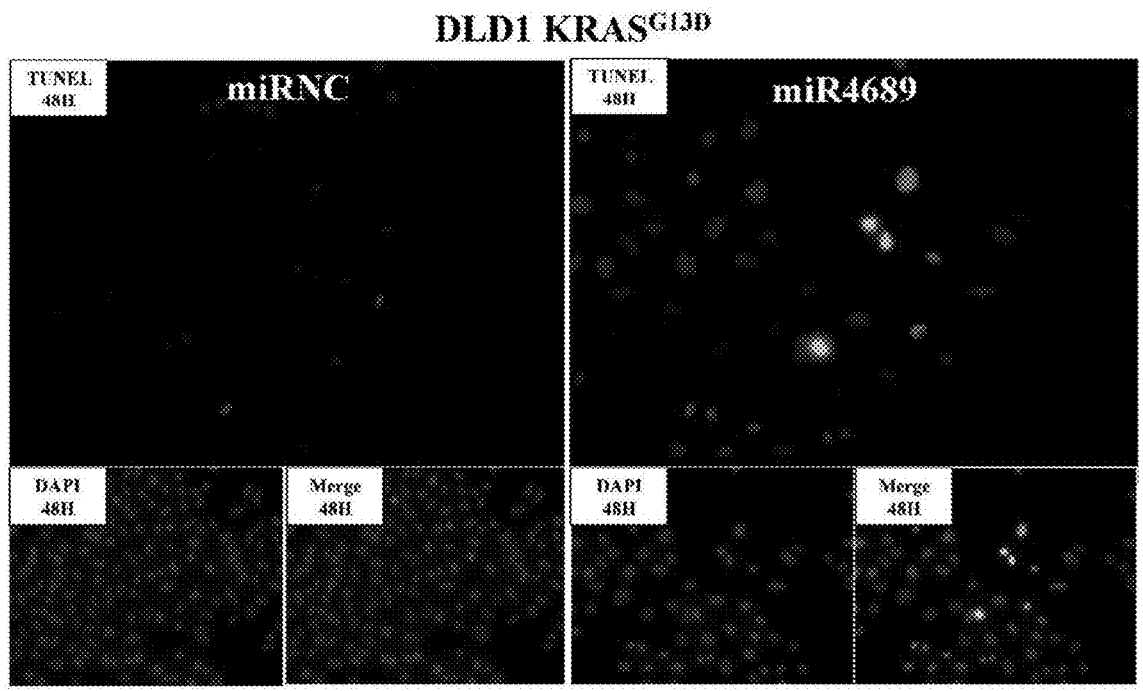
FIG. 18 shows results of Example 5, showing detection of apoptosis by the TUNEL method in DLD1 cells into which miR4689 was introduced.

The results of Western blotting are shown in FIGS. 16 and 17. The results of measurement of the expression level of the microRNA are shown in FIG. 16. The results of detection of apoptosis by the TUNEL method are shown in FIG. 18. These results clearly indicated that miR4689 suppressively acted on at least 2 separate pathways downstream of RAS, such as pMEK, MEK, pERK, pAKT, and AKT, in KRAS mutant colorectal cancer cells. It was also clearly indicated that miR4689 induced apoptosis in KRAS mutant-colorectal cancer cells.

Example 6: Analysis of miR4689 Expression Levels in Colorectal Cancer

In human colorectal cancer cells, expression levels of miR4689 were measured. In this test, 9 types of human colorectal cancer cells were used. Among these, 4 types had a mutated KRAS (G12V) gene, and 3 types had a mutated BRAF gene (V600E). Specific procedure included RNA extraction with an miReasy kit, reverse transcription with a TaqMan MicroRNA RT Kit (Applied Biosystems, Foster City, Calif.), and then real-time quantitative PCR with TaqMan MicroRNA Assays (Applied Biosystems) and 7500HT Sequence Detection System (Applied Biosystems).

Figure 19:
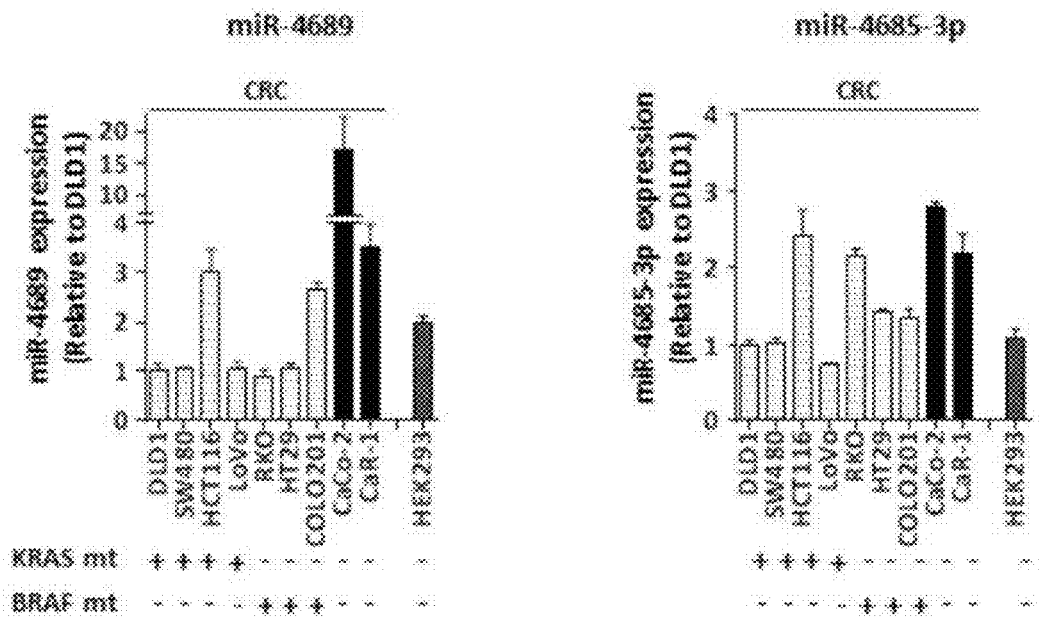
FIG. 19 shows measurement results of Example 6, showing expression levels of miR4689 and miR4685-3p in various human colorectal cancer cell lines.

The results are shown in FIG. 19. These results showed that colorectal cancer cell having the wild-type KRAS gene or the wild-type BRAF gene had a significantly higher expression of miR4689 than the mutated KRAS mutant or BRAF mutant colorectal cancer cells (p=0.02).

miR4689 expression levels were also measured in colorectal cancer cells derived from patients with colorectal cancer (46 cases) that had the wild-type KRAS gene or the mutated KRAS gene. The method of measuring expression levels of miR4689 was the same as described above.

Figure 20:
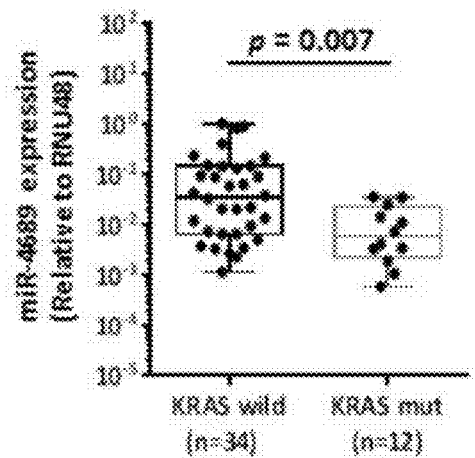
FIG. 20 shows results of Example 6, comparing expression levels of miR4689 in carcinoma tissue derived from patients with wild-type-KRAS colorectal cancer and in carcinoma tissue derived from patients with KRAS mutant colorectal cancer.

The results are shown in FIG. 20. These results showed that miR4689 in the colorectal cancer cell having the mutated KRAS gene was downregulated compared to that in the colorectal cancer cell having the wild-type KRAS gene.

The expression levels of miR4689 was also measured in normal large-intestine epithelial cells and colorectal cancer cells both derived from patients with colorectal cancer (44 cases). The method of measuring the expression amount of miR4689 was the same as described above.

Figure 21:
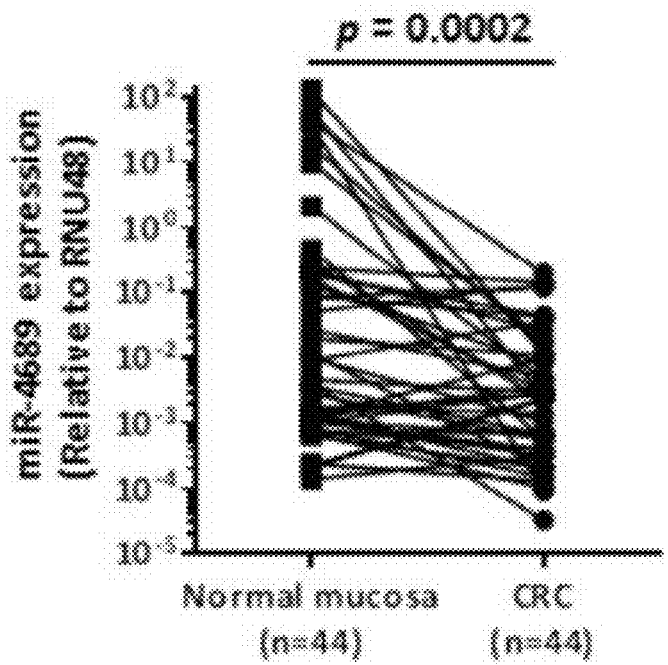
FIG. 21 shows measurement results of Example 6, comparing expression levels of miR4689 in normal colorectal epithelial cells and cancer cells both derived from patients with colorectal cancer.

The results are shown in FIG. 21. These results clearly showed a tendency that the expression level of miR4689 in the colorectal cancer cells was lower than in the normal cells (p=0.0002).

Example 7: Analysis of Relationship Between KRAS and miR4689 Expression

In order to evaluate the relationship between KRAS and miR4689 expression in cells in which expression levels of KRAS were increased by introduction of a mutated KRAS gene, the following test was conducted.

First, a mutated KRAS gene (G12V, SEQ ID NO: 3) was inserted into the SgfI-MluI site of a pCMV6 Empty Vecter shown in FIG. 1 to prepare a G12Vkras mt plasmid. Then, the resulting G12Vkras mt plasmid was introduced into normal human cells [HEK293 (human embryonic kidney cell), MRC5 (human embryonic lung cell)] with Lipofectamine 2000), and, as a result, mutated-KRAS-gene-introduced cells was prepared. As a control, a pCMV6 Empty Vecter into which no mutated KRAS gene was inserted was introduced into normal human cells, and, as a result, control cells were prepared. As for the resulting mutated-KRAS-gene-introduced cells and the resulting control cells, the expression levels of KRAS and the expression amount of miR4689 were measured. Measurement of KRAS expression levels was performed by Western blotting. Measurement of miR4689 expression levels was performed by qRT-PCR.

Figure 22:
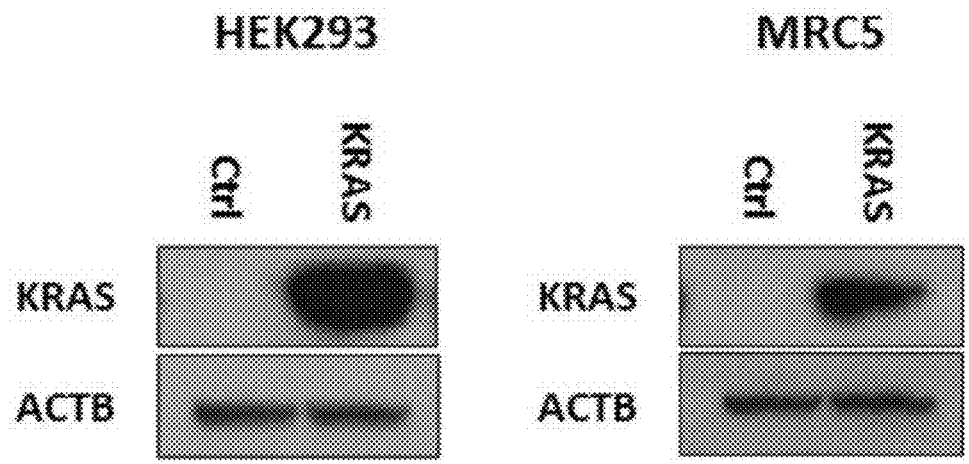
FIG. 22 shows measurement results of Example 7, showing expression levels of KRAS in mutated-KRAS-gene-introduced cells.
Figure 23:
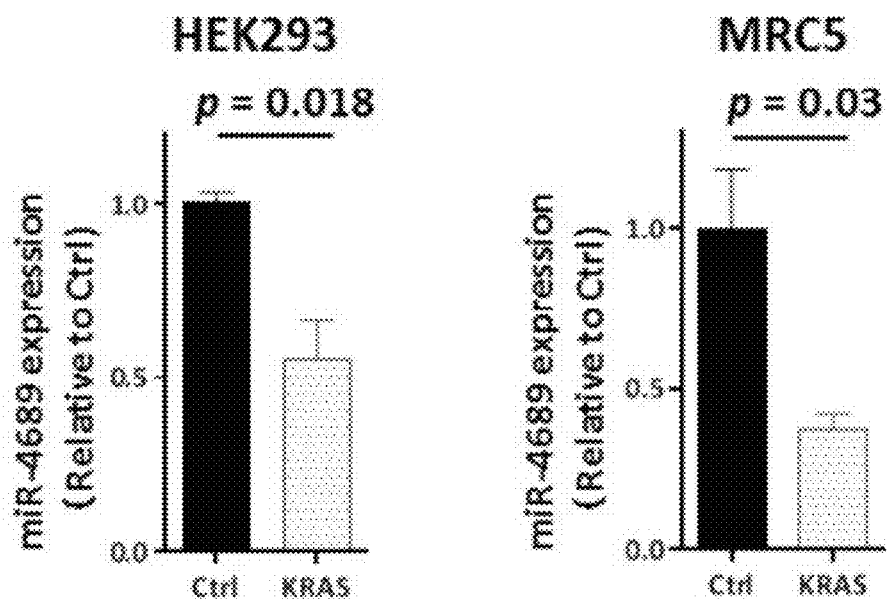
FIG. 23 shows measurement results of Example 7, showing expression levels of miR4689 in mutated-KRAS-gene-introduced cells.

The results are shown in FIGS. 22 and 23. These results showed that increases in KRAS expression caused decreases in miR4689 expression in the normal human cells, clearly indicating that there was an inverse relationship between KRAS and miR4689 expression.

Example 8: Analysis of miR4689 Expression Levels, Phosphorylation Capacity of ERK. and Cell Proliferation Properties in KRAS-Knockdown Colorectal Cancer Cells In order to evaluate the influence of KRAS knockdown on miR-4689 expression levels, phosphorylation capacity of ERK, and cell proliferation in colorectal cancer cells, the following test was conducted.

Into DLD1 cells (human colorectal cancer cell, having G13D mutation in the KRAS gene), an shRNA targeting KRAS (shKRAS: Broad Institute, Cambridge, Mass.) was introduced with a pLKO.1 vector. As a control, a pLKO.1 vector harboring a non-target shRNA (shCtrl) was introduced into a DLD1 cell.

Figure 24:
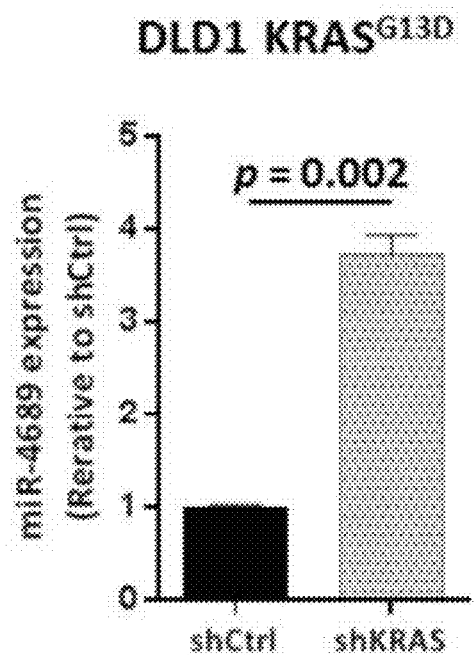
FIG. 24 shows measurement results of Example 8, showing expression levels of miR4689 in DLD1 cells into which shKRAS was introduced.

Expression levels of miR4689 in DLD1 cells with a shKRAS or shCtrl were measured by qRT-PCR. The results are shown in FIG. 24. The results showed that introduction of shKRAS into DLD1 cells increased miR4689 expression levels, which was in agreement with the results in Example A showing an inverse relationship between KRAS and miR4689 expression.

Figure 25:
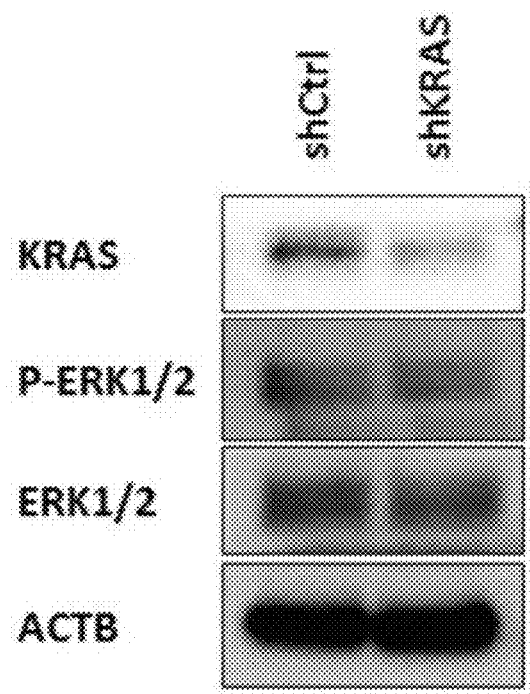
FIG. 25 shows measurement results of Example 8, showing expression levels of KRAS, P-ERK1/2, ERK1/2, and ACTB (loading control) in DLD1 cells into which shKRAS was introduced.

In addition, the expression levels of KRAS, P-ERK1/2, ERK1/2, and ACTB (loading control) in DLD1 cells with a shKRAS or shCtrl introduced thereinto were also measured by Western blotting. The results are shown in FIG. 25. These results showed that, in the DLD1 cell having shKRAS introduced thereinto, the expression amount of KRAS decreased while ERK phosphorylation was maintained.

Figure 26:
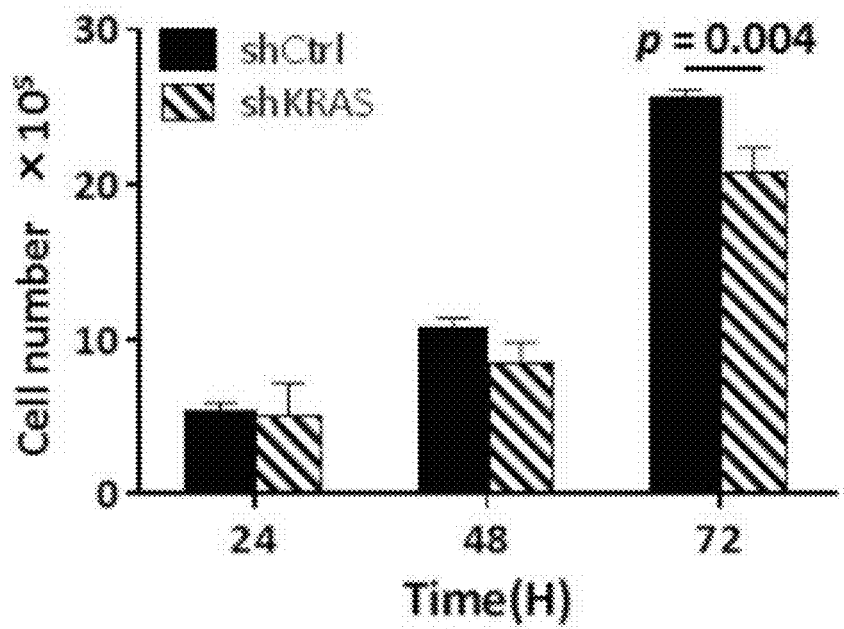
FIG. 26 shows results of Example 8, showing the results of proliferation assay of DLD1 cells into which shKRAS was introduced.

Furthermore, DLD1 cells with a shKRAS or shCtrl were subjected to a cell proliferation assay. Specific procedure was as follows. The cells were seeded in a 24-well plate at 5 to $6 \times 10^4$ cells/well, followed by culturing for 24 to 72 hours. The cells were counted 24, 48, and 72 hours after the culturing started. The results are shown in FIG. 26. These results showed that DLD1 cells having shKRAS introduced thereinto experienced a mild but significant suppressive effect on its proliferation after 72 hours of culturing, compared to the DLD1 cell having shCtrl introduced thereinto.

Example 9: Evaluation-1 of Therapeutic Effect on Colorectal Cancer Exhibited In Vivo by Complex Particles of miR4689 and Carbonate Apatite Particles In a medium/Matrigel solution that contained Matrigel (BD Biosciences, San Jose, Calif.) and medium at a volume ratio of 1:1, DLD1 cells were mixed at a proportion of $1 \times 10^6$ cells per 100 µL. The resulting mixture was subcutaneously injected into a female nude mouse (NIHON CLEA, Tokyo, Japan). into the left side and the right side of the lower back (100 µL each to the left and the right). On Day 0 when DLD1 cells were administered, and Day 0, 2, 4, 7, 9, 11, 14, and 16, a preparation including complex particles of miR4689 and carbonate apatite particles (sCa-miR-4689) to be obtained below was injected into the caudal vein, in an amount such that a single dose contained 40 µg of miR4689. As controls in this test, a case in which no complex particles of microRNA and carbonate apatite particles were introduced (Parent) and a case in which a control microRNA (SEQ ID NO: 5) was used instead of the microRNA (sCa-control-miR) were also tested under the same conditions.

(Method of Preparing Preparation Including Complex Particles of miR4689 and Carbonate Apatite Particles)

To 100 ml of distilled water, 0.37 g of $NaHCO_3$, 90 µl of $NaH_2PO_4 \cdot 2H_2O$ (1 M), and 180 µl of $CaCl_2$ (1 M) were added in this order for dissolution, followed by pH adjustment with 1 N HCl to pH7.5. The resulting mixture was filtrated through a filter with a diameter of 0.2 µm. To 1 ml of the resulting buffer, 2 µg of miR4689 and 4 µl of $CaCl_2$ (1 M) were mixed, followed by incubation in a water bath at 37° C. for 30 minutes. After centrifugation at 15000 rpm for 5 minutes, the resulting pellet was dispersed in physiological saline solution. As a result, a dispersion was obtained that contained complex particles in which miR4689 was contained within carbonate apatite particles. The resulting dispersion was subjected to ultrasonic vibration treatment for 10 minutes. As a result, a preparation was obtained that included a complex of miR4689 and carbonate apatite nanoparticles containing the miR4689. The ultrasonic vibration treatment was performed in a water bath having an ultrasonic vibration function, where a plastic container containing the dispersion obtained above was made floating in water at 20° C. in the water bath. The ultrasonic vibration treatment was continued for 10 minutes under conditions of a high-frequency power of 55 W and an oscillating frequency of 38 kHz. The resulting preparation was immediately subjected to the test described above. Measurement with a scanning probe microscope showed that the average particle size of the complex of miR4689 and carbonate apatite nanoparticles containing the miR4689 in the resulting preparation was 50 nm or less.

Figure 27:
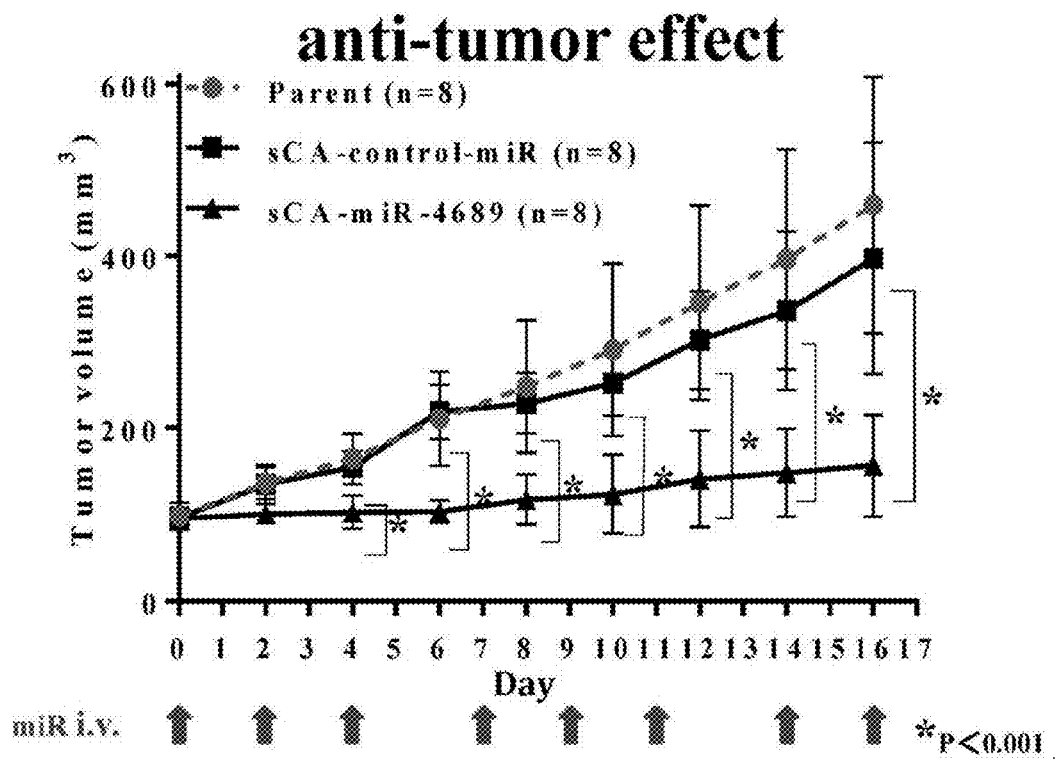
FIG. 27 shows results of Example 9 in a colorectal cancer cells, evaluating the influence of complex particles of miR4689 and carbonate apatite particles on the size of tumor.

From the point of time when DLD1 cells were administered, the size of tumor on the back of the mouse was measured with time (longer diameter×shorter diameter× shorter diameter×½). The results are shown in FIG. 27. The results showed that, when the complex particles of miR4689 and carbonate apatite particles were administered into the caudal vein, proliferation of DLD1 cells was significantly suppressed compared to that in the control. It was clearly indicated that, when administered in the form of complex particles of miR4689 and carbonate apatite particles, miR4689 exhibited a significantly excellent antitumor effect on colorectal cancer cells having a mutated KRAS gene.

Example 10: Evaluation-2 of Therapeutic Effect on Colorectal Cancer Exhibited In Vivo by Complex Particles of miR4689 and Carbonate Apatite Particles In a medium/Matrigel solution that contained Matrigel (BD Biosciences, San Jose, Calif.) and medium at a volume ratio of 1:1, DLD1 cells were mixed at a proportion of 1×10$^6$ cells per 100 μL. The resulting mixture was subcutaneously injected into a female nude mouse (NIHON CLEA, Tokyo, Japan), into the left side and the right side of the lower back (100 μL each to the left and the right). On Day 6, 7, 8, and 9, with the day of administration of DLD1 cells being regarded as Day 0, a preparation including complex particles of miR4689 and carbonate apatite particles used in Example 7 was injected into the caudal vein, in an amount such that a single dose contained 50 μg of miR4689. As controls in this test, a case in which no complex particles of microRNA and carbonate apatite particles was introduced (Parent) and a case in which a control microRNA (SEQ ID NO: 5) was used instead of the microRNA (sCa-control-miR) were also tested under the same conditions.

On Day 9 after administration of DLD1 cells, tumor tissues were resected, followed by measurement of miR4689 expression levels and Western blotting to measure the expression of apoptotic marker molecules. Specific procedure of the measurement of miR4689 expression levels included RNA extraction with an miREasy kit, reverse transcription with a TaqMan MicroRNA RT Kit (Applied Biosystems. Foster City, Calif.), and then real-time quantitative PCR with TaqMan MicroRNA Assays (Applied Biosystems) and 7500HT Sequence Detection System (Applied Biosystems).

Figure 28:
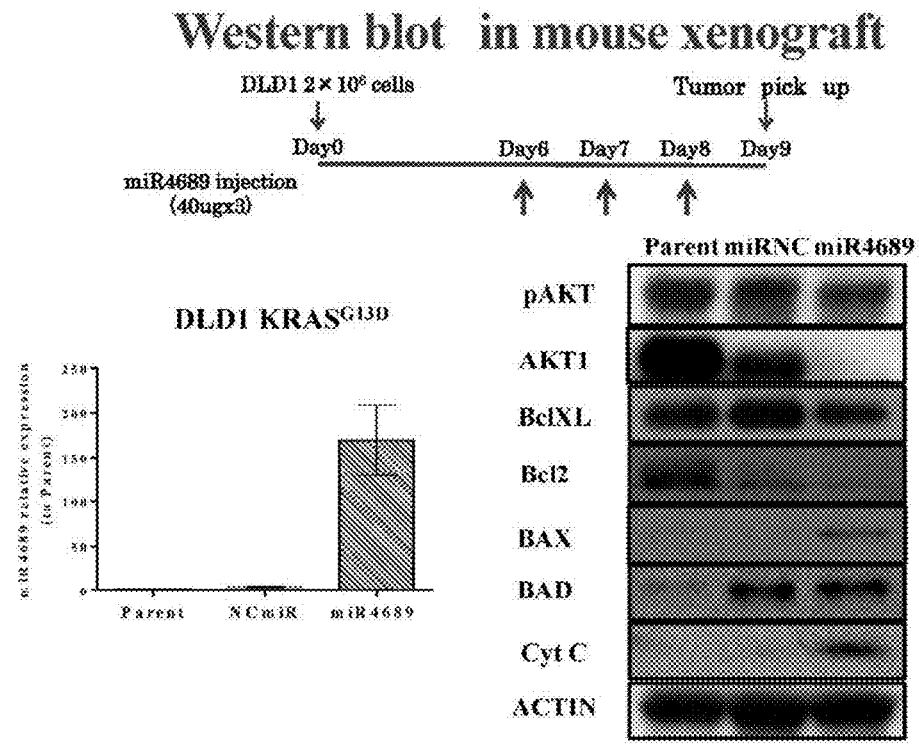
FIG. 28 shows results of Example 10, evaluating the influence of administration of complex particles of miR4689 and carbonate apatite particles on expression levels of miR4689 and apoptotic markers in colorectal cancer cells.

The results are shown in FIG. 28. These results showed that, in tumor tissues. administration of the complex particles of miR4689 and carbonate apatite particles caused increases in miR4689 expression, decreases in AKT, Bcl2, and BclXL expression, and increases in BAX expression, indicating that apoptosis of cancer cells was induced.

Example 11: Analysis of miR4689 Target Genes

The examples above suggested that miR4689 suppressed activation of the Ras/MEK/MAPK pathway. In this test, target genes of miR4689 in the Ras/MEK/MAPK pathway were examined.

First, the base sequence of miR4689 was compared with the base sequences of genes involved in the Ras/MEK/MAPK pathway. The result suggested, as shown in FIG. 29 A, that there was a sequence imperfectly complementary to the sequence of miR4689 (binding site of miR4689) in the 3'UTR region of KRAS present upstream within the Ras/MEK/MAPK pathway.

In order to check if one of the target genes of miR4689 is actually KRAS, the following test was conducted. First, a base sequence (SEQ ID NO: 6) harboring the imperfect complementary sequence (binding site) was amplified by PCR, and an insert nucleic acid was prepared. This insert nucleic acid was introduced into downstream of luciferase in the pmirGLO Dual-Luciferase miRNA Target Expression Vector (Promega), between the restriction enzyme sites Sal I and Xho I. Thus, pmirGLO-KRAS3'UTR vector was prepared. In D-MEM medium (containing FBS in an amount of 10% by volume) within a 96-well plate, 1×10$^4$ DLD1 cells were seeded, followed by overnight culture at 37° C. Subsequently, pmirGLO-KRAS3'UTR vector and miR4689 were added in an amount of 100 ng/well and 5 pmol/well, respectively, followed by culturing with 0.5 μl/well of Lipofectamine 2000 at 37° C. for transfection. 48 hours after transfection, the expression level of luciferase was measured by Dual Luciferase reporter Assay. For comparison, a test was conducted on a control microRNA (miR-NC, SEQ ID NO: 4) instead of miR4689, under the same conditions.

Figure 29:
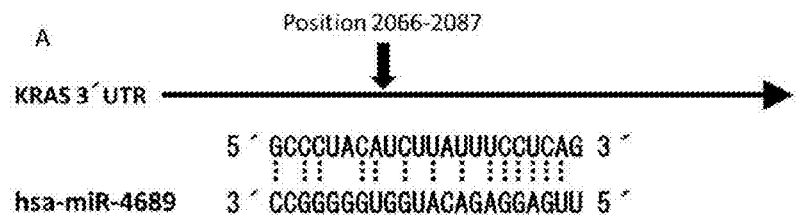
FIG. 29 A is a schema suggesting that there is a sequence imperfectly complementary to the sequence of miR4689 (SEQ ID NO: 1), (binding site of miR4689, SEQ ID NO: 8) in the 3'UTR region of KRAS present upstream within the Ras/MEK/MAPK pathway, and FIG. 29 B shows results of Example 11, evaluating the influence of miR4689 on luciferase activity in DLD1 cells into which pmirGLO-KRAS3'UTR vector was introduced.
Figure 29:
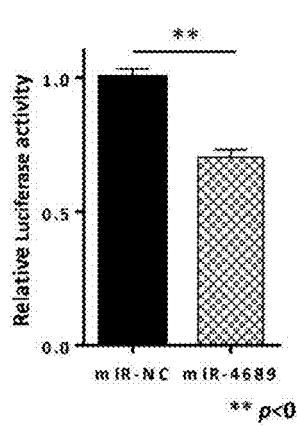

The results are shown in FIG. 29 B. In FIG. 29 B, expression levels of luciferase are shown as a relative value where the expression level of luciferase with miR-NC addition is regarded as 1. As clearly shown in FIG. 29 B, expression level of luciferase was suppressed when transfection with miR4689 was performed. In other words, it was clearly shown that one of the target genes of miR4689 was KRAS and that miR4689 bound to the 3UTR region of KRAS and regulated the translation.

These results showed that one of the target genes of miR4689 was KRAS. Next, KRAS protein and mRNA levels in colorectal cancer cells having miR4689 introduced thereinto were measured. Specific procedure was as follows. In D-MEM medium (containing FBS in an amount of 10% by volume) within a 6-well plate, 2×10$^5$ DLD1 cells (human colorectal cancer cells, having G13D mutation in the KRAS gene) or 2×10$^5$ SW480 cells (human colorectal cancer cells, having G12V mutation in the KRAS gene) were seeded, followed by overnight culture at 37° C. Subsequently, the microRNA was added thereto to achieve a concentration of 50 nM, followed by culturing with 5 μl/well of Lipofectamine IMAX at 37° C. for transfection. Then, the medium was exchanged to D-MEM medium (containing FBS in an amount of 10% by volume), followed by culturing. Western blotting was performed 48 hours after transfection, and KRAS protein expression was measured. In addition, 48 hours after transfection, KRAS mRNA expression was measured by qRT-PCR. For comparison, a test was conducted in the same manner on a control microRNA (SEQ ID NO: 5, miR-NC) instead of miR4689.

Figure 30:
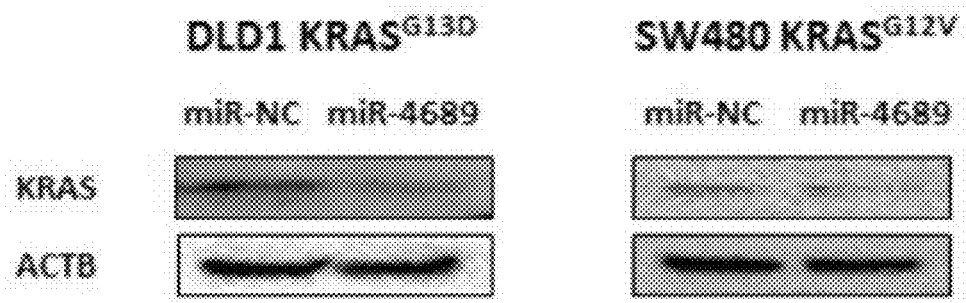
FIG. 30 shows measurement results of Example 11, showing expression of KRAS protein in colorectal cancer cells into which miR4689 was introduced.
Figure 31:
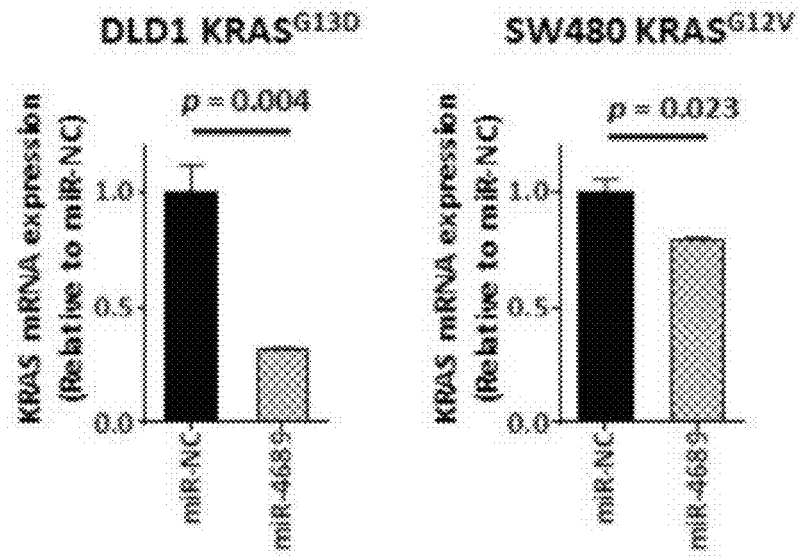
FIG. 31 shows measurement results of Example 11, showing KRAS mRNA levels in colorectal cancer cells into which miR4689 was introduced.

The results of measurement of KRAS protein expression are shown in FIG. 30, and the results of measurement of KRAS mRNA expression are shown in FIG. 31. These results showed that both KRAS protein and mRNA expression deceased in colorectal cancer cells having miR4689 introduced thereinto, supporting the prediction that one of the target genes of miR4689 was KRAS.

Example 12: Analysis of miR4689 Target Genes

The examples above suggested that miR4689 suppressed activation of the PI3K/Akt pathway. In this test, target genes of miR4689 in the PI3K/Akt pathway were examined.

First, the base sequence of miR4689 was compared with the base sequences of genes involved in the PI3K/Akt pathway. The result suggested, as shown in FIG. 32A, that there was a sequence imperfectly complementary to the sequence of miR4689 (binding site of miR4689) in the CDS of AKT1 in the PI3K/Akt pathway.

In order to check if one of the target genes of miR4689 is actually AKT1 the following test was conducted. First, a base sequence (SEQ ID NO: 7) harboring the imperfect complementary sequence (binding site) was amplified by PCR, and an insert nucleic acid was prepared. This insert nucleic acid was introduced into downstream of luciferase in a pmirGLO Dual-Luciferase miRNA Target Expression Vector (Promega), at the restriction enzyme sites Sal I and Xho I. Thus, a pmirGLO-AKT1CDS vector was prepared. In D-MEM medium (containing FBS in an amount of 10% by volume) within a 96-well plate, $1 \times 10^4$ DLD1 cells were seeded, followed by overnight culture at 37° C. Subsequently, the pmirGLO-AKT1CDS vector and miR4689 were added thereto in an amount of 100 ng/well and 5 pmol/well, respectively, followed by culturing with 0.5 µl/well of Lipofectamine 2000 at 37° C. for transfection. 48 hours after transfection, expression level of luciferase was measured by Dual Luciferase reporter Assay. For comparison, a test was conducted on a control microRNA (miR-NC. SEQ ID NO: 4) instead of miR4689, under the same conditions.

Figure 32:
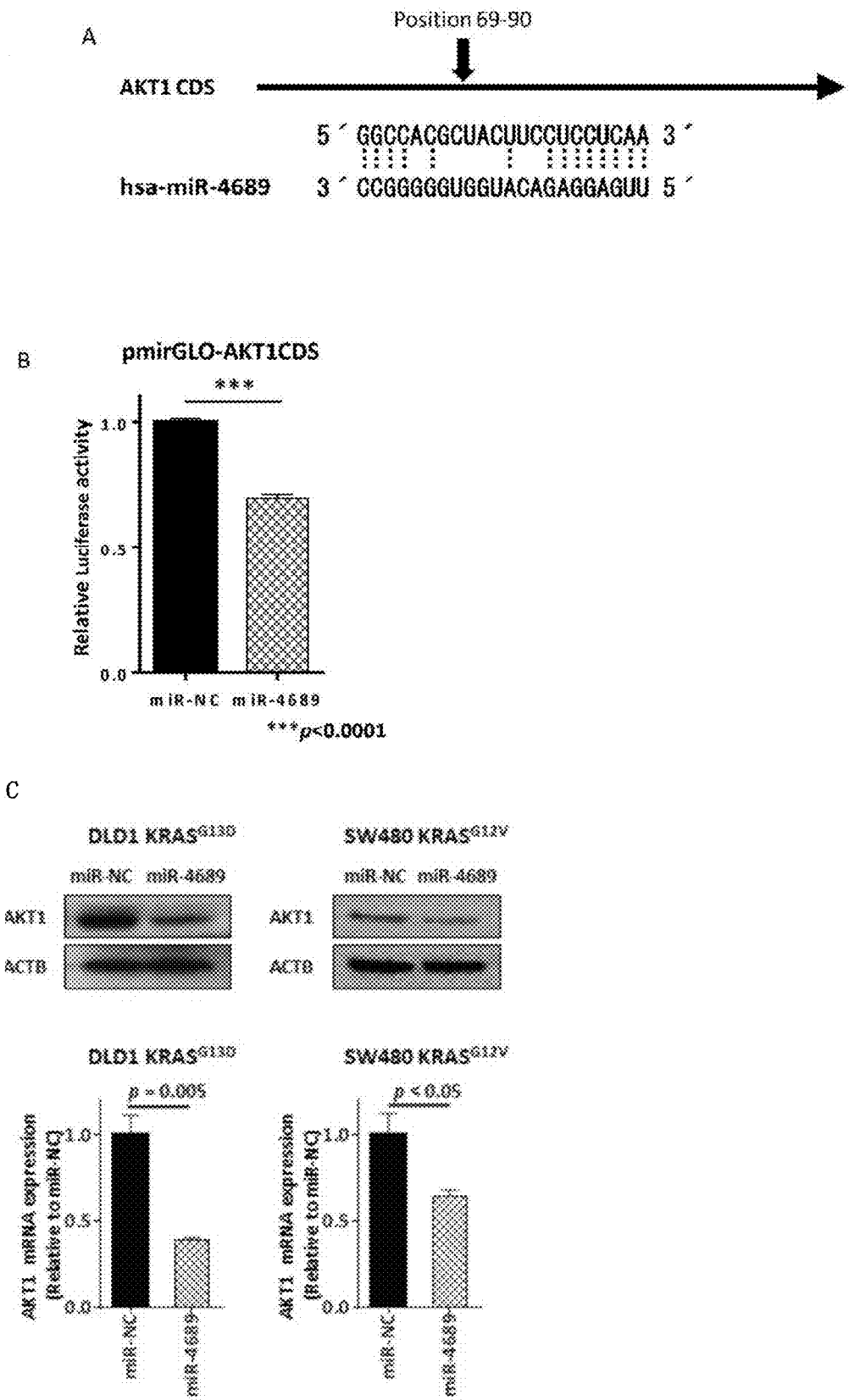
FIG. 32 A is a schema suggesting that there is a sequence imperfectly complementary to the sequence of miR4689 (SEQ ID NO: 1), (binding site of miR4689, SEQ ID NO: 9) in the CDS of AKT1 in the PI3K/Akt pathway, FIG. 32 B shows results of Example 12, evaluating the influence of miR4689 on luciferase activity in DLD1 cells into which a pmirGLO-AKT1CDS vector was introduced, and FIG. 32 C shows measurement results of Example 12, showing expression levels of Akt1 in protein and mRNA levels in DLD1 cells and SW480 cells into which miR4689 was introduced.

The results are shown in FIG. 32 B. In FIG. 32 B, expression levels of luciferase are shown as a relative value where the expression amount of luciferase with miR-NC addition is regarded as 1. As clearly shown in FIG. 32 B, expression level of luciferase was suppressed when transfection with miR4689 was performed. In other words, it was clearly shown that one of the target genes of miR4689 was AKT1 and that miR4689 bound to the CDS region of AKT1 and regulated translation.

Then, in D-MEM medium (containing FBS in an amount of 10% by volume) within a 6-well plate, $2 \times 10^5$ DLD1 cells (human colorectal cancer cells, having G13D mutation in the KRAS gene) or $2 \times 10^5$ SW480 cells (human colorectal cancer cells, having G12V mutation in the KRAS gene) were seeded, followed by overnight culture at 37° C. Subsequently. miR4689 was added thereto to achieve a concentration of 50 nM, followed by culturing with 5 µl/well of Lipofectamine IMAX at 37° C. for transfection. Western blotting was performed 48 hours after transfection, and Akt1 protein expression was measured. In addition, 48 hours after transfection, Akt1 mRNA expression in DLD1 cells and SW480 cell was measured by qRT-PCR. For comparison, a test was conducted on a control microRNA (miR-NC, SEQ ID NO: 4) instead of miR4689, under the same conditions.

The results are shown in FIG. 32 C. As clearly shown in FIG. 32 C, Akt1 expression deceased in DLD1 cells and the SW480 cell due to miR4689 transfection. In other words, these results also indicated that one of the target genes of miR4689 was Akt1.

Example 13: Analysis of Relationship that Apoptosis Induction in Colorectal Cancer Cells has with KRAS and Akt1

The examples above indicated that miR4689 targeted KRAS and Akt1 as its target genes and was effective in treating colorectal cancer. In order to check if a therapeutic effect on colorectal cancer would still be exhibited by knockdown of only one of KRAS and Akt1, the following test was conducted.

Into DLD1 cells, a shRNA targeting KRAS (shKRAS: Broad Institute. Cambrige, Mass.) was introduced with the use of a pLKO.1 vector. For comparison, a pLKO.1 vector harboring a non-target shRNA (shCtrl) was introduced into DLD1 cells.

Into DLD1 cells, a siRNA targeting Akt1 (siAkt1; Origene Technology, Rockville, Md., USA) was transfected with Lipofectamine. For comparison, a non-target siRNA (siCtrl) was transfected with Lipofectamine.

The DLD1 cells having the shRNA or the siRNA introduced thereinto was subjected to Western blotting, and the expression levels of apoptotic markers were measured.

Figure 33:
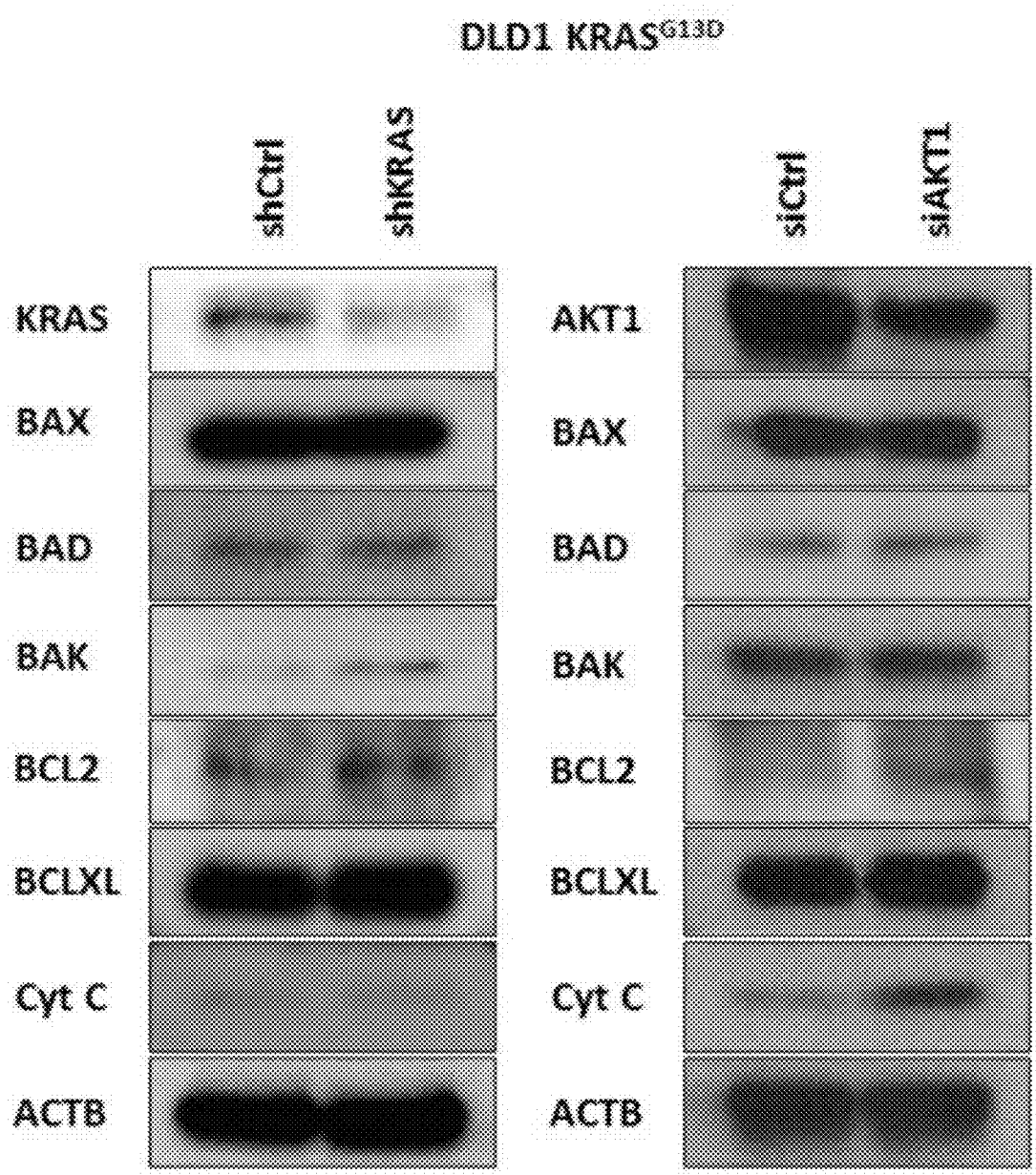
FIG. 33 shows measurement results of Example 13, showing expression levels of apoptotic markers in DLD1 cells into which shKRAS or siAkt1 was introduced.

The results are shown in FIG. 33. These results showed that increases in the expression levels of apoptotic markers were limited when only one of KRAS and Akt1 was knocked down, suggesting that induction of apoptosis by miR4689 in colorectal cancer cells was caused by knockdown of both KRAS and Akt1 genes.

Example 14: Analysis of Relationship that Apoptosis Induction in Colorectal Cancer Cells has with KRAS and Akt1

Into DLD1 cells, a different combination of miR4689, a control microRNA (SEQ ID NO: 5, miR-NC). a vector harboring a mutated KRAS gene, and a vector harboring the Akt1 gene was transfected with Lipofectamine 2000.

Figure 34:
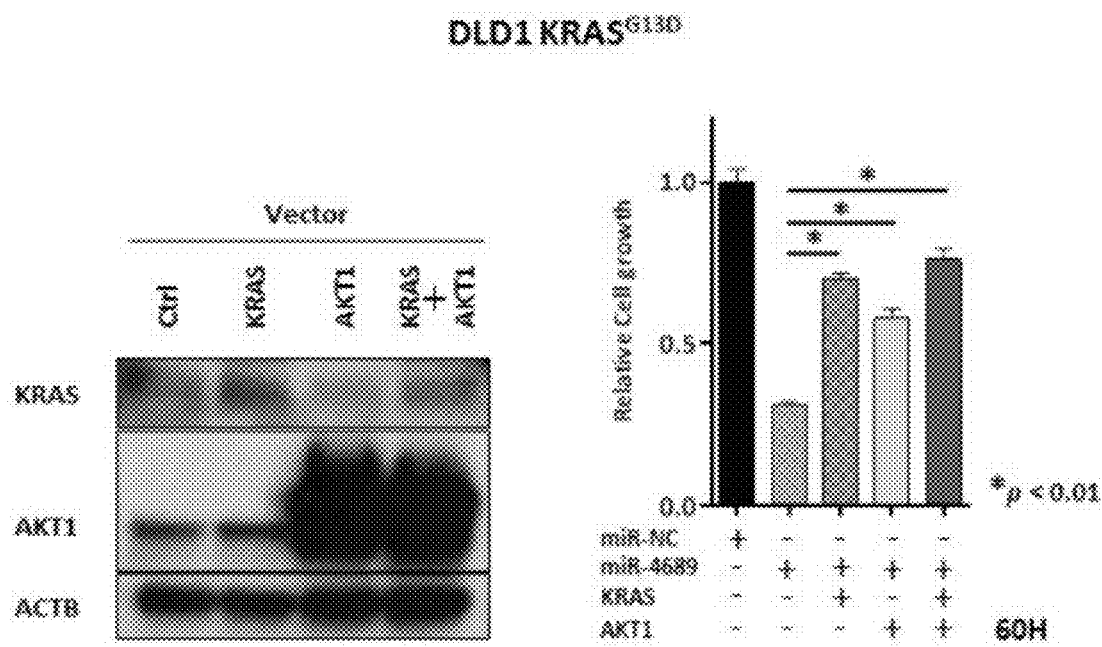
FIG. 34 shows results of Example 14, showing the measurement of expression levels of KRAS and Akt1 in DLD1 cells into which one of various combinations of miR4689, a control microRNA, a mutated KRAS gene, and the Akt1 gene was introduced, and also showing the results of a cell proliferation assay.

Western blotting was performed 48 hours after introduction, and KRAS and Akt1 protein expression were measured. In addition, each cells were subjected to a cell proliferation assay. Specific procedure was as follows. Each cell was seeded in a 24-well plate at 5 to $6 \times 10^4$ cells/well, followed by culturing for 16 hours. The cells were counted 60 hours after introduction of each vector or microRNA. The results are shown in FIG. 34. As shown in FIG. 34, in DLD1 cells overexpressing KRAS and/or Akt1, the suppressive effect of miR4689 introduction on cell proliferation was restored. In other words, these results also indicated that suppression of proliferation of colorectal cancer cells by miR4689 was caused by knockdown of both KRAS and Akt1 genes.

Example 15: Evaluation of In Vivo Safety of miR4689

In order to evaluate safety of miR4689, the following test was conducted. The preparation including complex particles of miR4689 and carbonate apatite particles used in Example 7 was injected into the caudal vein of a carcinoma-free female nude mouse (NIHON CLEA, Tokyo. Japan) in an amount such that a single dose contained 40 µg of miR4689, on Day 1, 2, 4, 6, 8, 10, and 12. For comparison in this test, a case in which no complex particles were introduced (Parent) and a case in which complex particles of a control microRNA (SEQ ID NO: 5) and carbonate apatite particles were also tested under the same conditions. The body weight of the nude mouse was measured with time. On Day 14, a blood chemical analysis and HE (Hematoxylin and Eosin) staining of organs were conducted.

Figure 35:
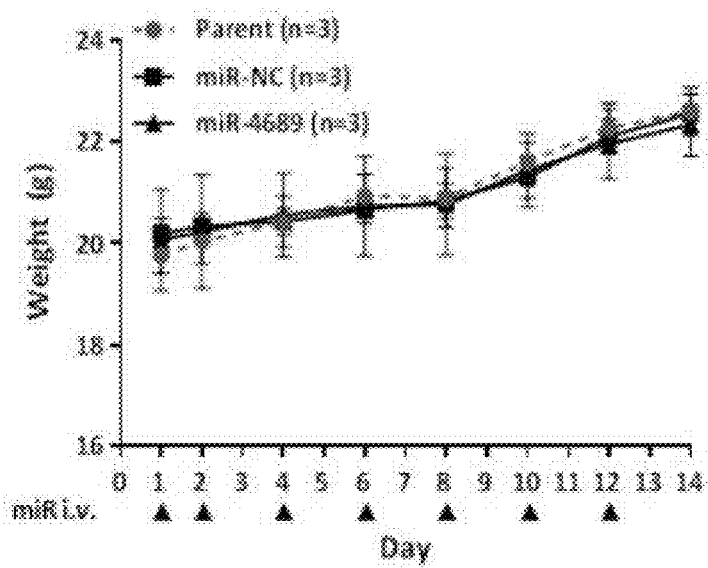
FIG. 35 shows results of Example 15, the time-course results of body weight of a carcinoma-free mouse that was administered with a preparation including complex particles of miR4689 and carbonate apatite particles.
Figures 36, 37:
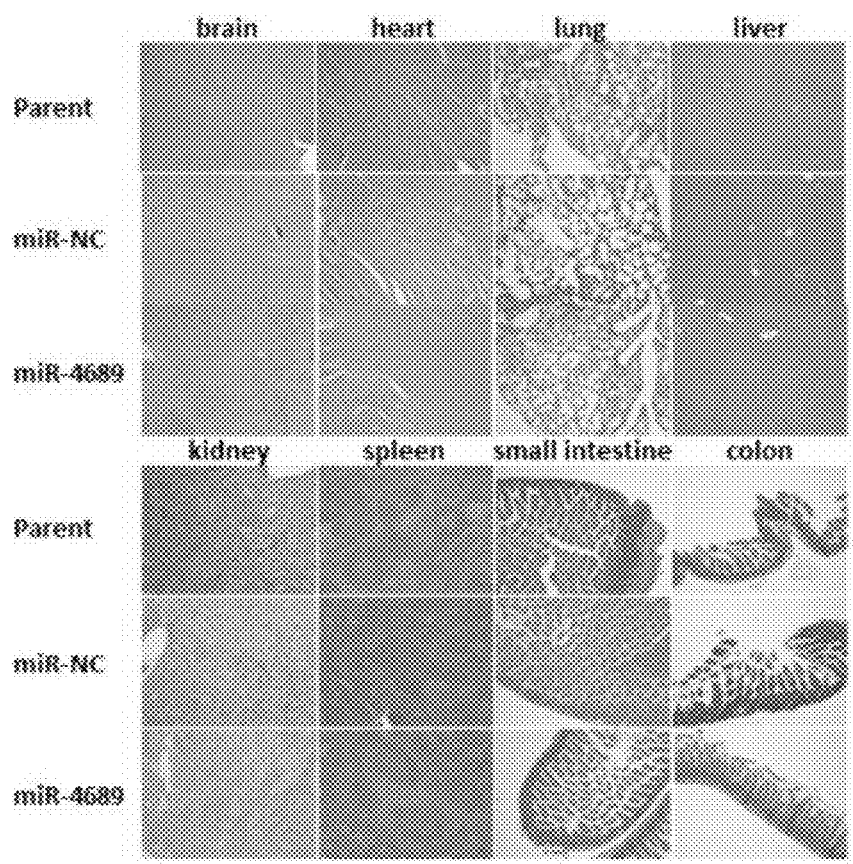
FIG. 36 shows results of Example 15, the results of blood chemical analysis in a carcinoma-free mouse that was administered with a preparation including complex particles of miR4689 and carbonate apatite particles.
FIG. 37 shows results of Example 15. the results of histological examination (HE staining) of each organ of a carcinoma-free mouse that was administered with a preparation including complex particles of miR4689 and carbonate apatite particles.

The time-course results of body weight are shown in FIG. 35. The results of the blood chemical analysis are shown in FIG. 36. The results of HE staining of various organs are shown in FIG. 37. In the group that received administration of the preparation including complex particles of miR4689 and carbonate apatite particles, no mice died and almost no change was observed in the body weight compared to the other group. The results of the blood chemical analysis showed no significant difference between the group that received administration of the preparation including complex particles of miR4689 and carbonate apatite particles and the other group. The results of the HE staining of various organs showed no histological damage sustained by the group that received administration of the preparation including complex particles of miR4689 and carbonate apatite particles. These results indicated that the complex particles of miR4689 and carbonate apatite particles had excellent safety.

Example 16: Analysis of Relationship Between miR4689 Expression and Prognosis in Patients with Colorectal Cancer Patients with Stage 0 to Stage IV colorectal cancer who undergone surgery were analyzed for miR4689 expression levels, the overall postsurgical 5-year survival rate, and clinicopathologic factors, by the following method. First, miR4689 expression levels were measured in colorectal cancer cells derived from patients with colorectal cancer (202 cases), and the median of miR4689 expression levels was determined. The patients were split into groups, namely, a high-miR4689-expressing group of patients who had miR4689 expression levels equal to or higher than the median and a low-miR4689-expressing group of patients who had miR4689 expression levels lower than the median. The method of measuring miR4689 expression levels was the same as described above. Then, the overall postsurgical 5-year survival rate of the patients with Stage 0 to Stage IV colorectal cancer was determined. Similarly, the postsurgical 5-year disease-free survival rate of the patients with Stage 0 to Stage III colorectal cancer was determined. In addition, the patients with Stage 0 to Stage III colorectal cancer were subjected to analysis for clinicopathologic factors, as well as to univariate analysis and multivariate analysis during the disease-free survival period (DFS).

Figure 38:
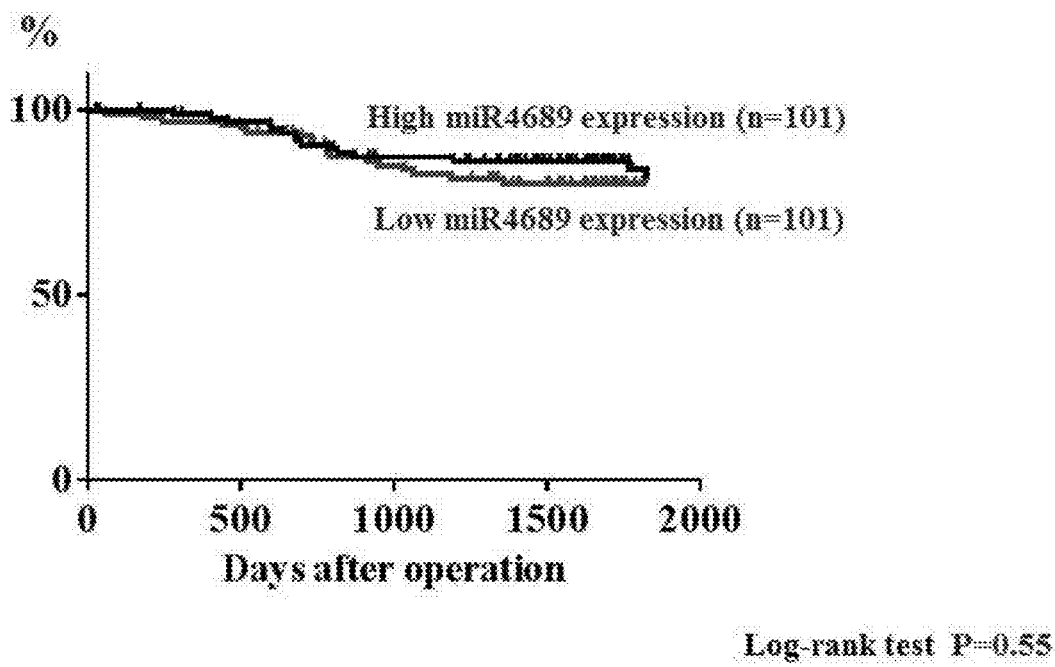
FIG. 38 shows results of Example 16, showing analysis of the overall postsurgical 5-year survival rate of patients with Stage 0 to Stage IV colorectal cancer, who were separated into a high-miR4689-expression group and a low-miR4689-expressing group.
Figure 39:
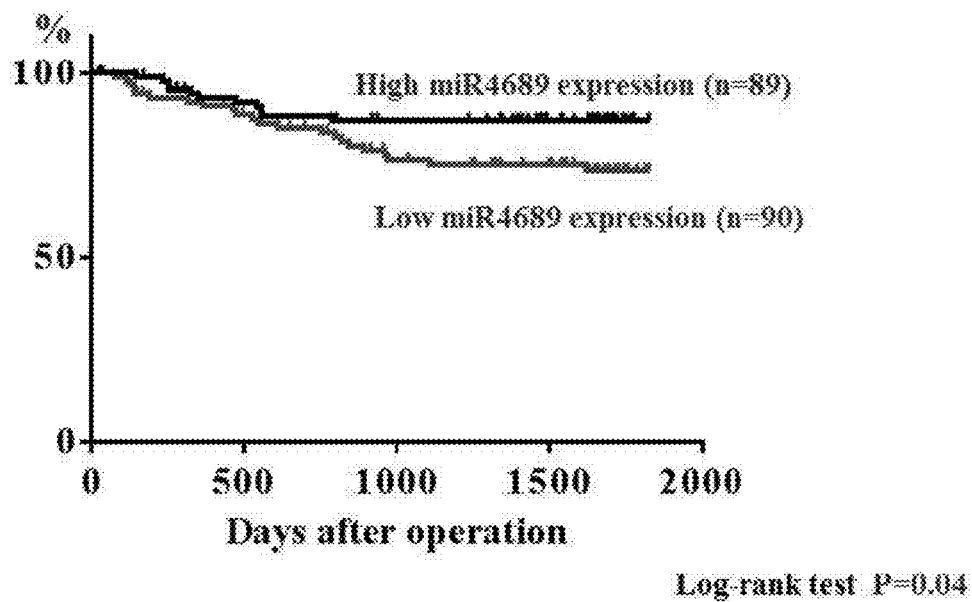
FIG. 39 shows results of Example 16, showing analysis of the postsurgical 5-year disease-free survival rate of patients with Stage 0 to Stage III colorectal cancer, who were separated into a high-miR4689-expression group and a low-miR4689-expressing group.

The overall postsurgical 5-year survival rate of the patients with Stage 0 to Stage IV colorectal cancer is shown in FIG. 38. The postsurgical 5-year disease-free survival rate of the patients with Stage 0 to Stage III colorectal cancer is shown in FIG. 39. The results of analysis of clinicopathologic factors are shown in Table 3. The results of univariate analysis and multivariate analysis during the disease-free survival period (DFS) are shown in Table 4. These results showed that the patients with colorectal cancer having high miR4689 expression had excellent postoperative prognosis compared to the patients with colorectal cancer having low miR4689 expression, suggesting that miR4689 replacement therapy can improve postoperative prognosis of patients with colorectal cancer.

TABLE 3

| Clinicopathologic factor | High-miR4689-expression group (N = 89) | Low-miR4689-expressing group (n = 90) | P VALUE |
|---|---|---|---|
| Sex | | | |
| Male/Female | 55/34 | 54/36 | NS |
| Tumor size (cm) (mean ± SD) | 5.0 ± 2.2 | 4.6 ± 1.9 | NS |
| Level of histological malignancy | | | |
| Well/Moderate | 82 | 87 | NS |
| Others | 7 | 3 | |
| Surface invasion in serosal layer Present/Absent | 33/56 | 44/46 | NS |
| UICC STAGE 0/I/II/III | 1/16/26/46 | 2/8/33/47 | NS |
| Lymphatic invasion Present/Absent | 47/42 | 57/33 | NS |
| Venous invasion Present/Absent | 46/43 | 40/50 | NS |
| Lymph node metastasis Present/Absent | 46/43 | 46/44 | NS |

NS: not significant

TABLE 4

| | Univariate analysis | | | Multivariate analysis | | |
|---|---|---|---|---|---|---|
| | RR | 95% CI | P value | RR | 95% CI | P value |
| Sex (Male/Female) | 0.94 | 0.43-2.1 | 0.87 | | | |
| Tumor size (≥5 cm/<5 cm) | 1.8 | 0.85-4.1 | 0.12 | | | |
| Level of histological malignancy (other/well, moderate) | 1.2 | 0.17-4.9 | 0.86 | | | |
| Surface invasion in serosal layer (Present/Absent) | 5.3 | 2.3-1.3.4 | <0.0001* | 4.2 | 1.8-10.8 | 0.001* |
| Venous invasion (Present/Absent) | 1.3 | 0.59-2.8 | 0.53 | | | |
| Lymph node metastasis (Present/Absent) | 3.5 | 1.5-8.7 | 0.003* | 2.9 | 1.2-7.5 | 0.02* |
| miR4689 Expression (Low/High) | 2.6 | 1.2-6.0 | 0.02* | 2.6 | 1.1-6.4 | 0.03* |

RR Relative risk
CI Confidence interval
*P < 0.05

The invention claimed is:

1. A method of treating a colorectal cancer, comprising a step of administering a therapeutically effective amount of either one or both of miR4689 and miR4685-3p to a patient with the colorectal cancer.

2. The method according to claim 1, wherein the colorectal cancer is a KRAS-gene-mutant colorectal cancer.

3. The method according to claim 2, wherein the KRAS-gene-mutant colorectal cancer comprises a RAS gene having amino acid substitution at either one or both of a codon 12 and a codon 13.

* * * * *